US009803164B2

(12) United States Patent
Mitchell

(10) Patent No.: US 9,803,164 B2
(45) Date of Patent: Oct. 31, 2017

(54) MEGAKARYOCYTE AND PLATELET PRODUCTION FROM STEM CELLS

(71) Applicant: New York Blood Center, Inc., New York, NY (US)

(72) Inventor: Beau W. Mitchell, Long Island, NY (US)

(73) Assignee: NEW YORK BLOOD CENTER, INC., New York, NY (US)

( * ) Notice: Subject to any disclaimer, the term of this patent is extended or adjusted under 35 U.S.C. 154(b) by 0 days.

(21) Appl. No.: 14/854,480

(22) Filed: Sep. 15, 2015

(65) Prior Publication Data

US 2016/0002586 A1 Jan. 7, 2016

Related U.S. Application Data

(63) Continuation-in-part of application No. 13/422,413, filed on Mar. 16, 2012.

(60) Provisional application No. 62/050,639, filed on Sep. 15, 2014, provisional application No. 62/089,139, filed on Dec. 8, 2014, provisional application No. 61/454,415, filed on Mar. 18, 2011.

(51) Int. Cl.
*C12M 1/00* (2006.01)
*C12N 5/078* (2010.01)

(52) U.S. Cl.
CPC ............ *C12M 23/58* (2013.01); *C12M 29/04* (2013.01); *C12M 47/02* (2013.01); *C12N 5/0644* (2013.01); *C12N 2500/02* (2013.01); *C12N 2501/125* (2013.01); *C12N 2501/145* (2013.01); *C12N 2501/21* (2013.01); *C12N 2521/00* (2013.01)

(58) Field of Classification Search
None
See application file for complete search history.

(56) References Cited

U.S. PATENT DOCUMENTS

2010/0248361 A1* 9/2010 Lasky .................. C12N 5/0644 435/355

OTHER PUBLICATIONS

Pallotta et al. "Three-dimensional system for the in vitro study of megakaryocytes and functional platelet production using silk-based vascular tubes", Tissue Engineering Part C: Methods 17(12): 1223-1232, published online Sep. 6, 2011.*
Nakagawa et al. "Two differential flows in a bioreactor promoted platelet generation from human pluripotent stem cell-derived megakaryocytes", Experimental Hematology 41: 742-748, published online Apr. 22, 2013.*
Eldor et al. "The effect of flow on the interaction of isolated megakaryocytes with subendothelial extracellular matrix", Blood Cells 17(3): 447-63, 1990.*

* cited by examiner

*Primary Examiner* — Emily Cordas
(74) *Attorney, Agent, or Firm* — K&L Gates LLP; Louis C. Cullman; Michelle Glasky Bergman

(57) ABSTRACT

Methods for obtaining purified populations of megakaryocytes and platelets by ex vivo culture of stem cells are provided herein.

20 Claims, 11 Drawing Sheets

100
102
110
140
120
122
124
126
135
160
130
150
138
180
170
175

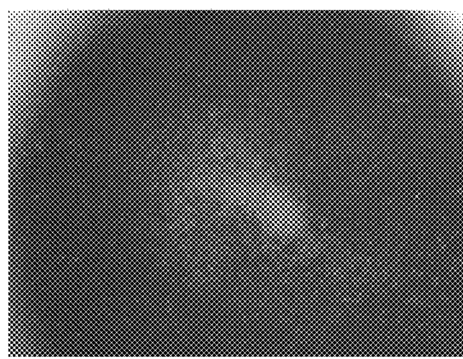
FIG. 2A
FIG. 2B
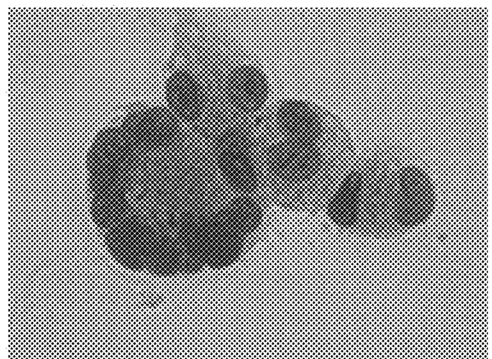
FIG. 3A
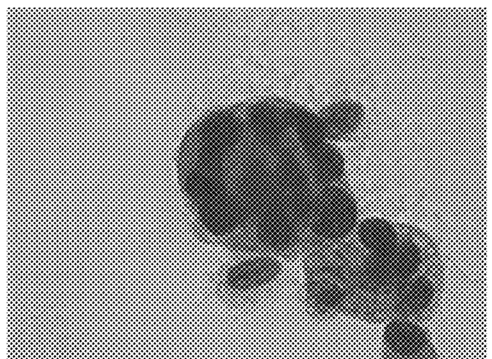
FIG. 3B

FIG. 9A
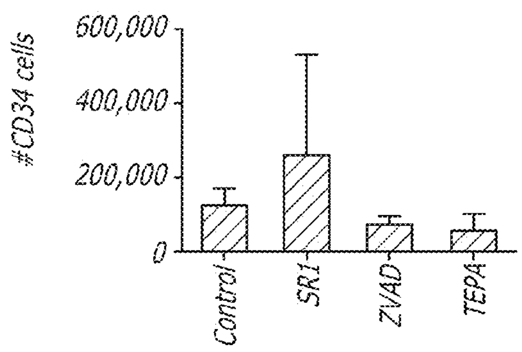
FIG. 9B
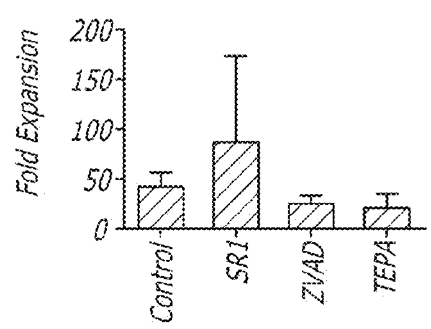
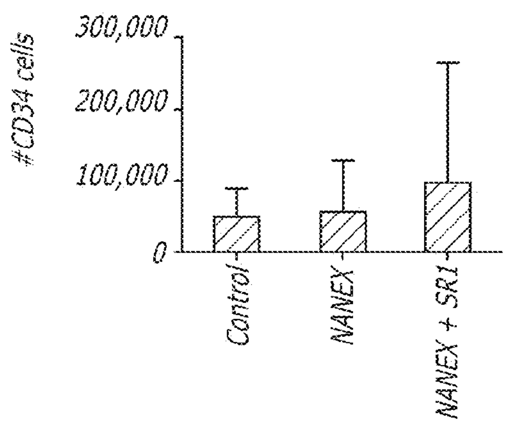
FIG. 9C
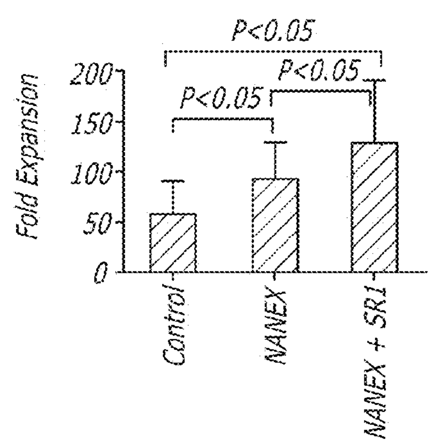
FIG. 9D

FIG. 10A
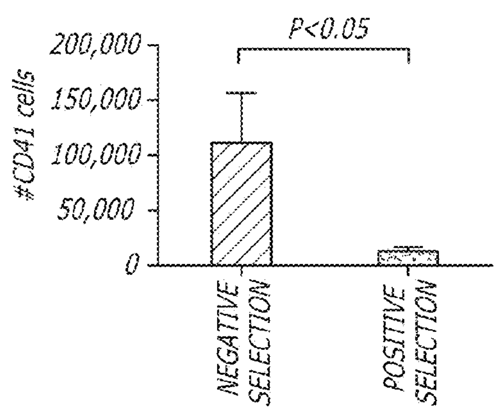
FIG. 10B
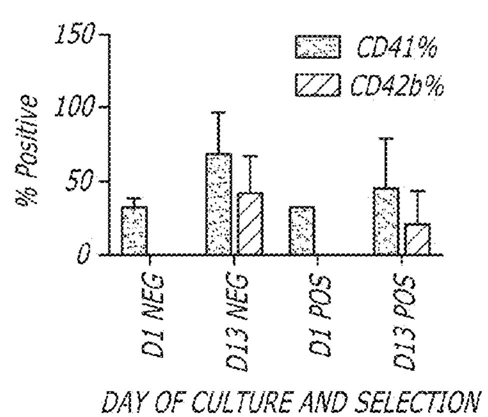
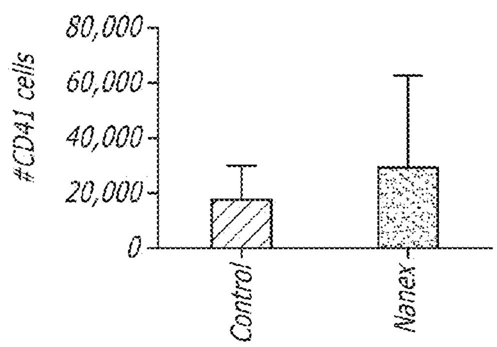
FIG. 10C
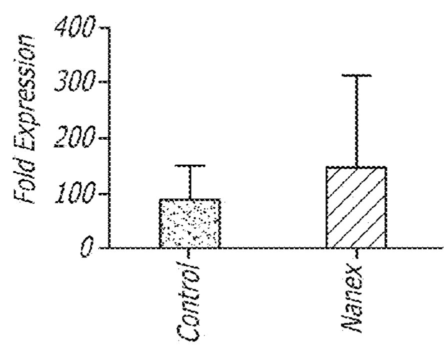
FIG. 10D

FIG. 11A
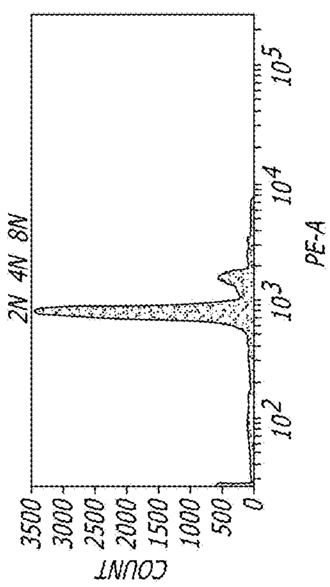
FIG. 11B
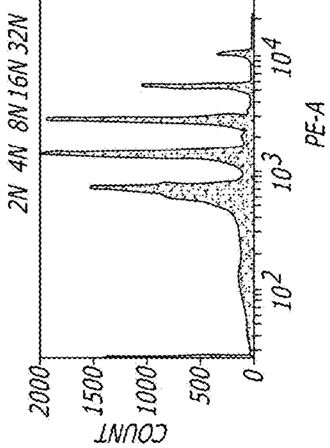
FIG. 11C
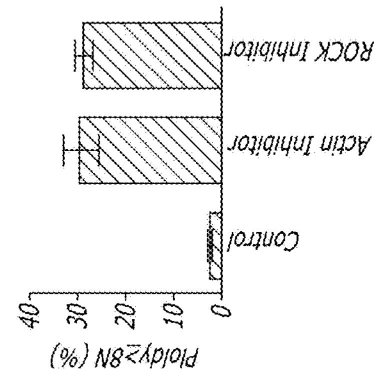
FIG. 11D
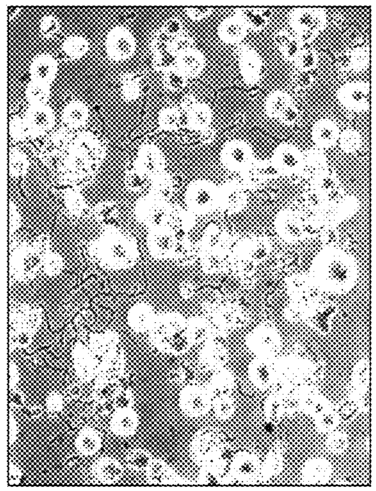
FIG. 11E
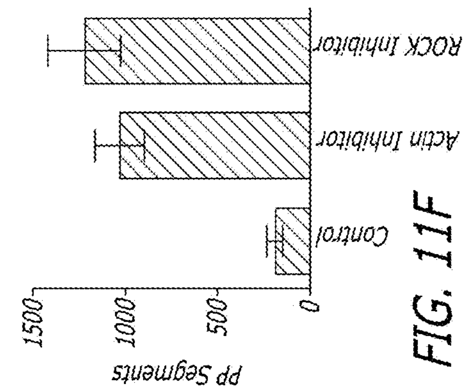
FIG. 11F

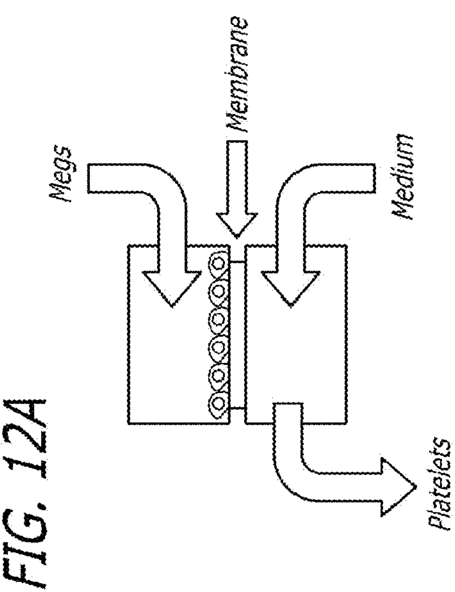
FIG. 12A
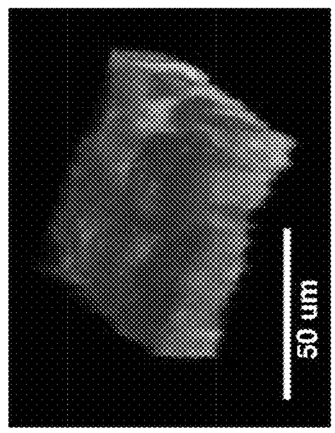
FIG. 12B
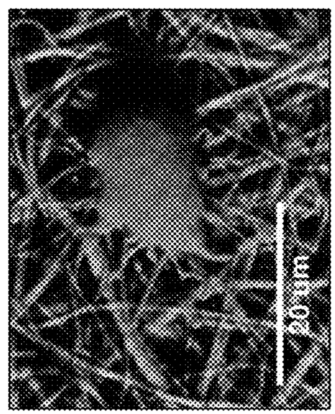
FIG. 12C
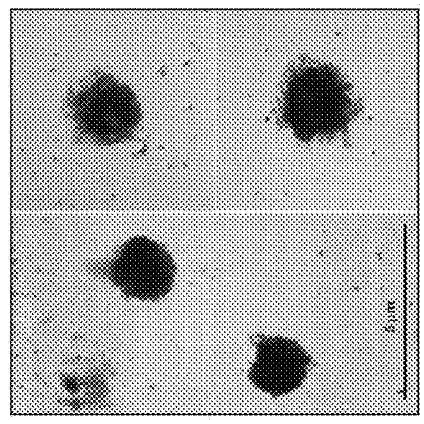
FIG. 12D
60
40
20
000
$-10^3$
0
$10^3$
$10^4$
$10^5$
PE-A
FIG. 12E

MEGAKARYOCYTE AND PLATELET PRODUCTION FROM STEM CELLS

CROSS-REFERENCE TO RELATED APPLICATIONS

This application claims the benefit under 35 U.S.C. §119 (e) of United States Provisional Patent Application Nos. 62/050,639 filed Sep. 15, 2014 and 62/089,139 filed Dec. 8, 2014 and claims priority to U.S. patent application Ser. No. 13/422,413 filed Mar. 16, 2012, which claims the benefit under 35 U.S.C. §119(e) of U.S. Provisional Patent Application 61/454,415 filed Mar. 18, 2011. The entire contents of these applications are incorporated by reference herein.

BACKGROUND

Field

The present disclosure is drawn to in vitro methods of producing platelets from stem cells for clinical use.

Description of the Related Art

Each year, millions of patients in the United States are affected by various blood disorders and diseases, such as thrombocytopenia (low platelet number), that require multiple treatments of platelet transfusions. Although more than 10 million platelet donations are made annually (all of which come from volunteer donors) the demand continues to increase at a greater rate than the supply. The process of obtaining platelets, however, is not only lengthy and costly, but it is further limited by a shelf life of only a few days. This short window of usability means that many donated platelet units are discarded before having an opportunity to serve the patients in need of these valuable products.

Platelets are tiny blood cells that perform the vital and highly specialized function of blood clotting. Almost a trillion platelets circulate in the average person's blood, and the turnover is such that the entire platelet population is replaced every 10 days. This represents a tremendous amount of ongoing platelet production. Platelets have a highly organized cytoskeleton and intracellular stores of over 300 proteins, which they secrete at sites of blood vessel injury. Platelets also play a role in inflammation, blood vessel growth, and tumor metastasis.

Platelets (thrombocytes) are small, irregularly shaped clear cell fragments 2-3 μm in diameter, which are derived from fragmentation of precursor megakaryocytes. Megakaryocytes are derived from hematopoietic stem cell precursor cells in the bone marrow These multipotent stem cells live in the marrow sinusoids and are capable of producing all types of blood cells depending on the signals they receive. The primary signal for megakaryocyte production is thrombopoietin (TPO). TPO induces differentiation of progenitor cells in the bone marrow towards a final megakaryocyte phenotype. The megakaryocyte develops through the following lineage: CFU-ME (pluripotential hemopoietic stem cell or hemocytoblast)→megakaryoblast→promegakaryocyte→megakaryocyte. The cell eventually reaches megakaryoblast stage and loses its ability to divide. However, it is still able to replicate its DNA and continue development, becoming polyploid. The cytoplasm continues to expand and the DNA complement can increase to greater than 64 N.

Once the cell has completed differentiation and becomes a mature megakaryocyte, it begins the process of producing platelets. TPO plays a role in inducing the megakaryocyte to form small proto-platelet processes. Platelets are held within these internal membranes within the cytoplasm of the megakaryocytes. There are two proposed mechanisms for platelet release. In one scenario, these proto-platelet processes break up explosively to become platelets. Alternatively, the cell may form platelet ribbons into blood vessels. The ribbons are formed via pseudopodia and they are able to continuously emit platelets into circulation. In either scenario, each of these proto-platelet processes can give rise to 2000-5000 new platelets upon breakup. Overall, more than 75% of these newly-produced platelets will remain in circulation while the remainder will be sequestered by the spleen.

Thrombocytopenia, a major medical problem affecting millions of patients per year in the US, can result in spontaneous bleeding and is treated using various methods to increase platelet production. The condition can result from malignancy and chemotherapy, immune disorders such as immune thrombocytopenia (ITP), infection, and major surgery. There are also a large number of inherited platelet defects that cause excessive bleeding. All of these serious medical conditions may require treatment at some point with life-saving platelet transfusions There has been much interest in the possibility of using stem cells to produce platelets in the laboratory for clinical use. Stem cells are undifferentiated cells in early stage of development and capable of giving rise to more cells of the same type or differentiating into a diverse range of cell lineages. The main different types of stem cells are human embryonic stem cells (HeSC), induced pluripotent stem cells (IPSC), and hematopoietic stem cells (HSC).

HeSC are pluripotent stem cells derived from the inner cell mass of an early-stage embryo and are capable of differentiating into all derivatives of the three primary germ layers: ectoderm, endoderm and mesoderm. These cells are capable of differentiating into all kinds of cells in the human body. IPSC are a type of pluripotent stem cell artificially derived from a mature cell. Typically, adult somatic cells are induced to become pluripotent by activating specific genes of immaturity in these cells. Hematopoietic stem cells are progenitor cells that circulate in the blood and reside in the bone marrow and have the potential to give rise to all hematopoietic cells. Hematopoietic stem cells can be acquired from the bone marrow, from peripheral blood with apheresis machines, or from umbilical cord or placenta after birth.

Culture systems have been described for differentiating stem cells into the various types of blood cells. There were expectations that stem cells, such as hematopoietic, HeSC and IPSC, could be used to generate blood cells for clinical use. Despite the successful production of functional platelets in the laboratory, reported yields have been far too low for clinical use and the field is currently at a technical impasse. As an example, one unit of umbilical cord blood may contain about $10^6$ (one million) CD34+ cells. One million CD34+ cells yield up to $10^7$ platelets under current optimal conditions. In contrast, a typical platelet transfusion delivers about $3\times10^{11}$ platelets. Thus, an increase in efficiency is needed to provide a transfusion of cultured platelets to equal the number of platelets from one unit of umbilical cord blood.

SUMMARY

Disclosed herein are methods and systems for the ex vivo production of megakaryocytes and platelets from stem cells.

In one embodiment disclosed herein, a method is provided for producing platelets in vitro comprising (1) selecting and culture-expanding megakaryocyte progenitor and/or stem cells, (2) differentiating the expanded cells into megakaryocytes, (3) maturing the megakaryocytes in an artificial bone marrow niche environment, (4) stimulating proplatelet formation and platelet release from the mature megakaryocytes, and (5) collecting the platelets. In another embodiment, the megakaryocyte progenitor and/or stem cells are selected from the group consisting of hematopoietic stem cells (from umbilical cord blood, peripheral and bone marrow), induced pluripotent stem cells (IPSC), human embryonic stem cells (HeSC), and human fibroblasts. Stem cells selected from these different sources are differentiated into megakaryocytes and stimulated to release platelets. In another embodiment, the stem cells are enriched for CD34+ cells prior to culture-expansion.

Optionally, mature megakaryocytes are isolated from the maturing culture and the mature megakaryocytes are used for platelet production and immature megakaryocytes are returning to the maturation culture.

In yet another embodiment, the stem cell expansion culture is conducted in the presence of a first growth medium comprising plurality of growth factors selected from the group consisting of aryl-hydrocarbon inhibitor/stem regenin-1, notch-ligand delta-1, prostaglandin-E2, Sal-like protein 4 (SALL4) gene activators, p38 inhibitors (such as SB203580), homeobox protein Hoxb4 activators, stromal cell-derived factor-1 (SDF-1α), histone acetyltransferase inhibitors (HAI, such as garcinol), valproic acid, co-culture with mesenchymal stem cells, endothelial and/or OP-9 (bone marrow-derived mouse stromal cells) cells, tropoelastin, copper chelation, benzyloxycarbonyl-Val-Ala-Asp (OMe) fluoromethylketone (Z-VAD-FMK), banana lectin, garlic lectin, interferon-α, thrombopoietin (TPO), stem cell factor (SCF), interleukin (IL)-3, IL-6, IL-11, FLT-3 ligand (FLT-3L), IGF-1, erythropoietin (EPO), dexamethasone, and lipids. In yet another embodiment, the growth factors are TPO, SCF, IL-3, IL-6, and IL-11.

In another embodiment, megakaryocyte expansion is conducted in a second medium comprising a plurality of growth factors selected from the group consisting of serotonin, arachidonic acid, Z-VAD-FMK, TPO, SCF, IL-3, IL-6, and FLT-3L.

Megakaryocyte maturation (polyploidization) is conducted in a cell growth matrix and a third medium comprising a plurality of growth factors selected from the group consisting of nicotinamide, folic acid, vitamin B12, Rho/Rock inhibitors, Src inhibitors, Aurora-B inhibitors, Bcr-Abl inhibitors, phorbol 12-myristate 13-acetate (PMA), blebbistatin, a stathmin inhibitor (staurosporine), myosin light chain kinase (MLCK) inhibitors, and, under conditions of increased oxygen concentration, between about 10% and about 30% $PO_2$. In another embodiment second the cell growth matrix is collagen I. In yet another embodiment, the growth factors are nicotinamide and a Rho/Rock inhibitor. In still another embodiment, the Rho/Rock inhibitor is Y27632.

In another embodiment, the proplatelet formation and platelet release steps are conducted in an artificial three-dimensional (3D) bone marrow niche environment. The 3D bone marrow niche environment is comprised of alginate or polystyrene beads, mesh, felt or other 3D structure, coated with a plurality of growth factors selected from the group consisting of fibrinogen, fibronectin, von Willebrand factor (vWF), Fas-ligand, PMA, nitric oxide, Rho/Rock inhibitors, Src inhibitors, Rac1 inhibitors, CDC42 inhibitors, SDF-1α, hirudin, heparin, c-Myc inhibitors, MLCK inhibitors, and Rho/Rock inhibitors. Shear stress is applied with a flow system (syringe pumps) to the 3-D matrix to improve platelet release. Tangential flow systems and membranes with 3-5 μm pores are also suitable.

Also disclosed herein are methods for producing platelets in vitro comprising (1) culturing stem cells in a first growth medium to produce a megakaryocyte progenitor cell population; (2) maturing the expanded megakaryocyte progenitor cells in an artificial bone marrow niche environment comprising a second growth medium in the presence of an oxygen concentration between about 10% and about 30% $PO_2$ to differentiate the megakaryocyte progenitor cells into megakaryocytes; (3) isolating the mature megakaryocytes; (4) culturing the mature megakaryocytes in a three-dimensional matrix and a third growth medium and in the presence of an oxygen concentration between about 10% and about 30% $PO_2$ and a flow rate of between about 100 and 55,000 μl/min to produce platelets; and (5) collecting the platelets.

In some embodiments, the stem cells are selected from the group consisting of hematopoietic stem cells, induced pluripotent stem cells, embryonic stem cells, and fibroblasts. In yet another embodiment, the hematopoietic stem cells are obtained from the bone marrow, peripheral blood, or cord blood. In another embodiment, the stem cells are enriched for CD34+ cells prior to culture-expansion.

In some embodiments, the first growth medium comprises a plurality of growth factors selected from the group consisting of aryl-hydrocarbon inhibitor/stem regenin-1, notch-ligand delta-1, prostaglandin-E2, SALL4 gene activators, Hoxb4 activators, stromal cell-derived factor-1 (SDF-1α), histone acetyl transferase inhibitors, valproic acid, co-culture with mesenchymal stem cells and/or OP-9 cells, tropoelastin, copper chelation, Z-VAD-FMK, banana lectin, garlic lectin, interferon-α, thrombopoietin (TPO), p38 inhibitors, stem cell factor (SCF), dexamethasone, lipids, IGF-1, erythropoietin (EPO), IL-3, IL-6, IL-11, and FLT-3 ligand (FLT-3L). In another embodiment, the growth factors are TPO, SCF, IL-3, IL-6, and IL-11.

In some embodiments, the second growth medium comprises a plurality of growth factors selected from the group consisting of serotonin, arachidonic acid, Z-VAD-FMK, TPO, SCF, IL-3, IL-6, FLT-3L, nicotinamide, and a Rho/Rock inhibitor. In another embodiment, the growth factors are nicotinamide and a Rho/Rock inhibitor.

In some embodiments, the cell growth matrix is selected from the group consisting of extracellular matrix extracts, extracellular matrix gels, gelatin, fibrinogen, collagen, methylcellulose, and combinations thereof.

In some embodiments, the artificial bone marrow niche further contains mesenchymal stem cells and/or endothelial cells.

In some embodiments, the third growth medium comprises a plurality of growth factors selected from the group consisting of fibrinogen, fibronectin, von Willebrand factor (vWF), Fas-ligand, PMA, nitric oxide, MLCK inhibitors, Rho/Rock inhibitors, Src inhibitors, SDF-1α, nicotinamide, folic acid, vitamin B12, Rho/Rock inhibitors, Src inhibitors, Aurora-B inhibitors, Bcr-Abl inhibitors, phorbol 12-myristate 13-acetate (PMA), blebbistatin, and MLCK inhibitors. In yet another embodiment, the growth factors are fibrinogen, fibronectin, vWF, Fas-ligand, a MLCK inhibitor and a Rho/Rock inhibitor.

Also disclosed herein is a platelet production system for the ex vivo production of platelets comprising: a bioreactor for expansion of stem cells in the presence of a first growth medium in fluid communication with a maturation chamber, the maturation chamber comprising an artificial bone marrow niche and a second growth medium, wherein the maturation chamber is in fluid communication with a cell separation chamber for selecting mature megakaryocytes, which is in fluid communication with a platelet production module, the platelet production module comprising one or more plurality of platelet production chambers, a three-dimensional matrix, a third growth medium, and a plurality of pumps for moving the third growth medium across the platelet production chambers, wherein the platelet production module is in fluid communication with; a platelet collection chamber.

Disclosed herein are various embodiments of platelet production systems for the ex vivo production of platelets. Such systems include: at least one fluid source, the fluid comprising a growth medium; at least one platelet production chamber in fluid communication with the at least one fluid source, the chamber comprising a first and a second fluid flow path, the first and second fluid flow paths separated from each other within the chamber by a permeable scaffold. In some embodiments, the permeable scaffold is configured to allow a plurality of megakaryocytes located in the first fluid path to extend their respective proplatelet processes through the permeable scaffold into the second fluid flow path. In some embodiments, the platelet production system is configured to force fluid from the fluid source into the at least one platelet production chamber. In some embodiments, the second fluid flow path brings the growth medium into contact with at least a portion of the permeable scaffold to remove at least some platelets from the proplatelet processes.

According to some embodiments of platelet production systems, the growth medium is pumped through the at least one platelet production chamber at a volumetric flow rate of between about 15 ml/min and about 55 ml/min. In some embodiments, the growth medium exhibits a shear rate at an interface with the permeable scaffold that is between about 1 $s^{-1}$ and about 100 $s^{-1}$. In some embodiments, the growth medium exhibits a shear rate at an interface with the permeable scaffold that is between about 1 $s^{-1}$ and about 500 $s^{-1}$. In some embodiments, the growth medium exhibits a shear rate at an interface with the permeable scaffold that is between about 1 $s^{-1}$ and about 40 $s^{-1}$. In some embodiments, the growth medium exhibits a shear rate at an interface with the permeable scaffold that is between about 30 $s^{-1}$ and about 70 $s^{-1}$. In some embodiments, the growth medium exhibits a shear rate at an interface with the permeable scaffold that is at least about 4 $s^{-1}$. In some embodiments, the growth medium exhibits a shear rate at an interface with the permeable scaffold that is less than about 10 $s^{-1}$.

According to some embodiments, the permeable scaffold is between about 100 μm and about 200 μm in thickness. In some embodiments, the permeable scaffold includes pores that are between about 2 μm and about 5 μm. In some embodiments, the platelet production systems disclosed herein are configured so that the growth medium follows both the first and the second fluid flow path. In some embodiments, the flow rate of the growth medium through the first flow path is less than the flow rate of the growth medium through the second flow path. In some embodiments, the flow rate of the growth medium through the first flow path is greater than the flow rate of the growth medium through the second flow path. In some embodiments, the flow rate of the growth medium through the first flow path is sufficient to hold at least some of the plurality of megakaryocytes against the permeable scaffold and to compel at least some of the proplatelet process of the megakaryocytes to grow in the direction of the second fluid flow path.

Also disclosed herein are methods of growing and harvesting platelets from proplatelet processes, the methods including: providing a production system for the ex vivo production of platelets, the production system comprising: at least one fluid source, the fluid comprising a growth medium; at least one platelet production chamber in fluid communication with the at least one fluid source, the chamber comprising a first and a second fluid flow path, the first and second fluid flow paths separated from each other within the chamber by a permeable scaffold, the permeable scaffold configured to prevent a mature megakaryocyte from passing through; pumping the growth medium through at least one of the first and second flow paths; providing a plurality of megakaryocytes within the first fluid flow path so as to lodge the megakaryocytes against the permeable scaffold and direct their respect proplatelet processes in the direction of the second fluid flow path; removing the growth medium from the second flow path after it has interacted with at least a portion of the permeable scaffold so as to remove at least some platelets from at least some of the proplatelet processes.

According to some embodiments, the disclosed methods achieve a 10-fold to 1,000-fold increase in platelet production. In some embodiments, the increase in platelet production is between 50-fold and 500-fold, between 50-fold and 300-fold, or between 70-fold and 200-fold.

In some embodiments of the methods disclosed herein, the growth medium is pumped through the at least one platelet production chamber at a volumetric flow rate of between about 0.1 ml/min and about 55 ml/min. In some embodiments, the growth medium exhibits a shear rate at an interface with the permeable scaffold that is between about 1 $s^{-1}$ and about 40 $s^{-1}$. In some embodiments, the growth medium exhibits a shear rate at an interface with the permeable scaffold that is between about 30 $s^{-1}$ and about 70 $s^{-1}$. In some embodiments, the growth medium exhibits a shear rate at an interface with the permeable scaffold that is at least about 4 $s^{-1}$ or at least about 20 $s^{-1}$. In some embodiments, the growth medium exhibits a shear rate at an interface with the permeable scaffold that is less than about 10 $s^{-1}$ or less than about 80 $s^{-1}$. In some embodiments, the permeable scaffold is between about 100 μm and about 200 μm in thickness. In some embodiments, the permeable scaffold includes pores that are between about 2 μm and about 5 μm. In some embodiments, the system is configured so that the growth medium follows both the first and the second fluid flow path. In some embodiments, the flow rate of the growth medium through the first flow path is less than the flow rate of the growth medium through the second flow path.

These and other features are disclosed in greater detail in the accompanying figures and the Detailed Description below.

BRIEF DESCRIPTION OF THE DRAWINGS

FIGS. 2A and B depict cultures of hematopoietic stem cells.

FIGS. 3A and B depict megakaryocytes differentiated from the culture in FIG. 2.

FIG. 9A illustrates in numbers the expansion of CD34 cells from cord blood after 7 days of culture with SR-1, zVADfmk or TEPA compared to control. Starting number: 10,000 total cells.

FIG. 9B illustrates the fold-expansion of CD34 cells from cord blood after 7 days of culture with SR-1, zVADfmk or TEPA compared to control. Starting number: 10,000 total cells.

FIG. 9C illustrates in numbers the expansion of CD34 cells cultured on NANEX membrane with or without addition of SR-1 compared to control. Starting number: 1,000 total cells. SR-1: stem regenin-1, TEPA: tetraethylenepentamine.

FIG. 9D illustrates the fold-expansion of CD34 cells cultured on NANEX membrane with or without addition of SR-1 compared to control. Starting number: 1,000 total cells. SR-1: stem regenin-1, TEPA: tetraethylenepentamine.

FIG. 10A illustrates in numbers the expansion of CD41 cells from CD34 cells derived from UCB after 10 days of culture after using either negative or positive selection of CD34 cells. Starting number: 10,000 cells.

FIG. 10B illustrates the percent of CD41 and CD42b after 10 days of culture after either negative or positive selection of CD34 cells.

FIG. 10C illustrates the number of CD41 cells cultured on NANEX membrane compared to control. Starting number: 1,000 cells.

FIG. 10D illustrates the fold-expression of CD41 cells cultured on NANEX membrane compared to control. Starting number: 1,000 cells.

FIG. 11A illustrates a flow cytometry plot of ploidy analysis in control on day 11 of culture.

FIG. 11B illustrates a flow cytometry plot of latrunculin-treated CD41 cells on day 11 of culture.

FIG. 11C illustrates quantitation of the proportion of cells with ploidy 8N or higher after treatment with latrunculin or Y27632.

FIG. 11D illustrates a micrograph showing proplatelet formation in a control culture.

FIG. 11E illustrates a micrograph showing proplatelet formation in a latrunculin-treated culture.

FIG. 11F illustrates a quantitation of proplatelet formation in latrunculin or Y27632 treated cultures.

FIG. 12A illustrates a schematic of a bioreactor according the present disclosure showing flow pattern and position of the membrane.

FIG. 12B is a fluorescence microscopy image of CD41 cells on a membrane after introduction into the bioreactor: CD41 (red) on the NANEX membrane (green autofluorescence), reconstruction from z-stack. Megakaryocytes after initiation of flow for 30 min showing processes passing into the membrane.

FIG. 12C is a fluorescence microscopy image of CD41 cells on a membrane after introduction into the bioreactor: CD41 (red) on the NANEX membrane (green autofluorescence), reconstruction from z-stack. Megakaryocyte after resting on the membrane for 30 min without flow, showing processes passing into the membrane.

FIG. 12D illustrates platelet-like particles produced in a bioreactor, Wright Giemsa stain.

FIG. 12E illustrates a flow cytometry showing P-selectin expression (x-axis) on the platelet like particles produced in the bioreactor: red represents isotype control, green represents non-activated platelets, blue represents platelets activated by phorbol myristate acetate.

DETAILED DESCRIPTION

Figure 1:
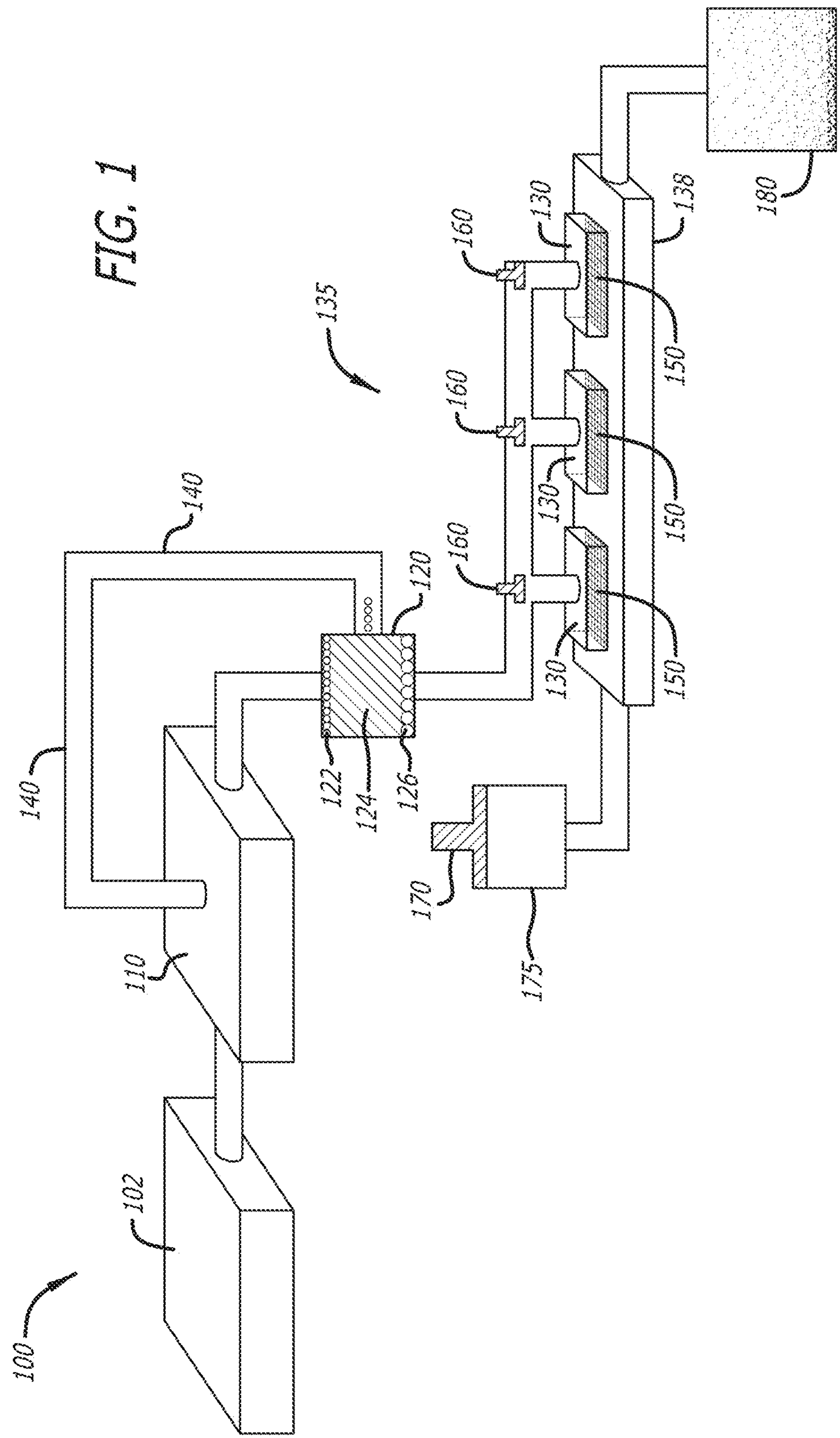
FIG. 1 depicts a diagram of a cell culture and expansion system for producing platelets in vitro.

The presently disclosed methods and systems are useful for the production of clinically useful quantities of megakaryocytes and platelets in vitro from different sources of progenitor or stem cells.

Several steps along the biological pathway from stem cell to platelet can be quantity limiting. For example, expansion of CD34 cells early in the culture process will have a greater impact on final cell number than expansion of later, more differentiated cells. Accordingly, in some embodiments, the authors of this disclosure have divided the process of megakaryocyte biogenesis and platelet production into modules focusing on those quantity-limiting steps. Quantity limiting steps include CD34 cell expansion, immature megakaryocyte expansion, polyploidization, and platelet release. In some embodiments, each of these steps are addressed individually and then assembled into a production line to achieve high platelet yields. In some embodiments, each of these steps are combined into a continuous production line so as to minimize contamination and the need for oversight. Thus, herein are described novel, stepwise culture methods and bioreactors that have the capability of producing clinically relevant numbers of platelets.

For the purposes of the present disclosure, the terms "stem cells" and "megakaryocyte progenitor cells" are interchangeable and refer to pluripotent, multipotent or unipotent stem cells or progenitor cells which are capable of differentiating into megakaryocytes and have the potential to produce platelets.

For the purposes of the present disclosure, the term "growth factors" refers to protein and non-protein factors which support the growth, maintenance, maturation, and differentiation of cells.

For the purposes of the present disclosure, the term "growth medium" refers to liquid or semi-solid aqueous medium which includes electrolytes, energy sources, growth factors and other materials necessary for the ex vivo culture of cells.

The process of platelet production from stem cells may be divided into several stages according to cell characteristics, internal cellular processes, and environmental signals. These stages include (1) stem cell replication; (2) megakaryocyte replication; (3) megakaryocyte maturation (increase in ploidy); (4) proplatelet formation; and (5) platelet release.

Each of these stages requires specific culture conditions and chemical factors to support the cell growth and differentiation. Factors involved in stage 1, hematopoietic stem cell (CD34+ cell) expansion include, but are not limited to, aryl-hydrocarbon inhibitor/stem regenin-1, notch-ligand/delta-1, prostaglandin-E2, SALL4 gene induction or addition of exogenous SALL4 protein, recombinant human Hoxb4, stromal cell-derived factor-1 (SDF-1α), valproic acid, co-culture with endothelial cells, mesenchymal stem cells and/or OP-9 cells, tropoelastin, copper chelation, p38 inhibitors (such as SB203580), histone acetyltransferase inhibitors (HAI) (such as garcinol), Z-VAD-FMK, banana lectin, garlic lectin, interferon-α, thrombopoietin (TPO), stem cell factor (SCF), IL-3, IL-6, IL-11, and FLT-3 ligand (FLT-3L). Long-term culture for CD34+ and megakaryocyte progenitor expansion is conducted with a combination of growth factors. In one non-limiting embodiment, the growth factors are SCF (10-400 ng/ml, such as 100 ng/ml), TPO (10-250 ng/ml, such as 50 ng/ml), IGF-1 (10-100 ng/ml, such as 40 ng/ml), EPO (0.5-5 μg/ml, such as 2 μg/ml), dexamethasone (0.2-3 such as 1 μM) and cholesterol-rich lipid mix (Sigma). Cells are cultured for approximately 4-14 days and progenitors are selected by density or size exclusion methods and replated for expansion. This process can be repeated several times until higher order progenitor expansion is achieved.

Factors involved in stage 2, megakaryocyte expansion include, but are not limited to, serotonin, arachadonic acid, Z-VAD-FMK, cell growth matrices such as MATRIGEL®, gelatin, fibrinogen, collagen, methylcellulose, and extracellular matrix gel, and cytokines such as TPO, SCF, IL-3, IL-6, and FLT-3L. Factors involved in stage 3, polyploidization/endomitosis include, but are not limited to: nicotinamide (vitamin B3), folic acid, vitamin B12, Rho/Rock inhibitors, Src inhibitors, stathmin inhibitor (staurosporine), Aurora-B inhibitors, Bcr-Abl inhibition, overexpression of cyclin D1, D3 and p19, phorbol 12-myristate 13-acetate (PMA), blebbistatin, MLCK inhibitors, and increased oxygen concentration between about 15% and about 30% $PO_2$. In alternative embodiments, the $PO_2$ is between about 15% and about 25%; in another embodiment, the $PO_2$ is between about 17% and about 22%; and in another embodiment the $PO_2$ is about 20%. Factors involved in stages 4 and 5, proplatelet formation and platelet release, include: fibrinogen, fibronectin, von Willebrand factor (vWF), Rho/Rock inhibitors, hirudin, heparin, Src inhibitors, Rac1 inhibitor, CDC42 inhibitor, Fas-ligand, PMA, nitric oxide, c-Myc inhibitors, and SDF-1α. Culturing cells in 3D matrices and applying shear stress with a flow system provides an improved environment for proplatelet formation and platelet release.

Various metrics can be used to determine the proper environment for growing proplatelet processes and detaching platelets from those proplatelet processes. The authors of the present disclosure have found that both shear stress and shear rate are useful metrics to use.

Fluid shear stress (τ) is created by fluid movement tangential to the face of a surface, for incompressible Newtonian fluids the shear stress will be linearly proportional to the velocity gradient perpendicular to the plane of shear. Shear stress is also is defined as the component of stress coplanar with a material cross section. Shear stress arises from the force vector component parallel to the cross section. Shear stress may be represented by any number of suitable formulas. For the purposes of the present disclosure, the following formula suffices:

$$\tau = \frac{F}{A}$$

where F is the force applied by the fluid, and A is the area of the surface against which the fluid applies a shearing force, the area being parallel to the applied force vector.

Shear rate (γ) and shear stress are related as follows:

$$\tau = \mu \cdot \dot{\gamma}$$

where μ is the dynamic viscosity of the fluid. However, rather than determine the value of μ or even the shear stress, for the sake of simplicity, the shear rate can be calculated using a few simple assumptions.

Shear rate is the rate at which a progressive shearing deformation is applied to some material. In the context of a pipe, particularly a cylindrical or circular-shaped pipe, shear rate is defined as follows at the inner wall of a pipe in which a Newtonian fluid is flowing:

$$\dot{\gamma} = \frac{8 \cdot v}{d}$$

where d is the inside diameter of the pipe and ν is the linear fluid velocity, which is defined as $$v = \frac{Q}{A}$$

with Q being the volumetric flow rate of the fluid and A being the cross-sectional area of the pipe, which is equal to pi multiplied by the radius squared, or $\pi \cdot r^2$. In other words, shear rate may be recast as follows:

$$\dot{\gamma} = \frac{4 \cdot Q}{\pi \cdot r^3}$$

Hematopoietic stem cells are recruited into the megakaryocyte lineage by the cytokine thrombopoietin. TPO induces the stem cells to produce megakaryocyte- and platelet-specific proteins and to undergo the process of growth into the giant megakaryocyte cell. The megakaryocyte matures in a specific environment, or niche, of the bone marrow, which sustains megakaryocyte maturation. This allows the megakaryocyte to remain in one place and mature in an environment that strongly inhibits platelet formation. The developing megakaryocyte is also functionally restrained from producing platelets while in the bone marrow niche. The matrix protein collagen 1 mediates both of these effects. The baseline state of cultured megakaryocytes also appears to be characterized by inhibition of platelet formation. This is important in the marrow so that the platelets are not produced at the wrong time and place. When the megakaryocyte matures and migrates toward the blood vessels, this inhibition is lifted and it releases its platelets.

Megakaryocytes have the remarkable characteristic of doubling their nuclear and cellular contents without cell division through a process called endomitosis. Through endomitosis, the megakaryocyte grows to enormous size and may have more than 64 times the normal nuclear contents. The increase of nuclear contents, or polyploidy, plays a fundamental role in the platelet formation by allowing the cell to produce the large amounts of proteins and organelles necessary for platelet formation and function. Importantly, mature megakaryocytes also have vast quantities of extra cell membrane with which to make platelets. Inducing polyploidization can be achieved using the following reagents alone or in different combinations.

Rho/Rock inhibitors. The final steps of cell division require regulation of actin and myosin to form the cleavage furrow and contractile ring. The inhibition of actin and myosin during cytokinesis allows megakaryocytes to replicate DNA material without undergoing cell division. The Rho/Rock pathway signals through myosin light chain (MLC) and filamin and activates both stress fibers and lamellipodia formation. Y27632 inhibits the Rho/Rock pathway and consequently inhibits myosin activation and the contractile ring formation, presumably allowing the megakaryocyte to undergo polyploidization. Exemplary Rho/Rock inhibitors include, but are not limited to, Y27632, thiazovivin, GSK429286A, fasudil HCl, Y39983, Wf-536, SLx-2119, Azabenzimidazole-aminofurazans, DE-104, and H-1152P.

Nicotinamide (NIC). Decreases in p53 activity are responsible for accelerated DNA synthesis, higher ploidy and delayed apoptosis. NIC increases p53 activity and thus increases endomitosis and megakaryocyte polyploidization.

Src inhibitors. The inhibition of Src family kinases increases megakaryocyte polyploidization through the Lyn/Fyn pathway and inhibition of actin polymerization. Exemplary Src inhibitors include, but are not limited to, saracatinib (AZD0530), bosutinib (SKI-606), danusertib (PHA-739358), NVP-BHG712, quercetin (sophoretin), PCI-32765, KX2-391, AP23846, and PP2.

Aurora-B inhibitors. Aurora-B is responsible for controlling the microtubules formation and consequent chromosome separation during mitosis. Its inhibition increases microtubule destruction through stathmin and mitotic centromere-associated kinesin (MCAK) action. Exemplary Aurora-B kinase inhibitors include, but are not limited to, AMG 900, AT9283, Aurora A Inhibitor I, AZD1152, AZD1152-HQPA (barasertib), CCT129202, CYC116, danusertib (PHA-739358), ENMD-2076, GSK1070916, hesperadin, JNJ-7706621, KW-2449, MLN8054, MLN8237 (alisertib), PF-03814735, PHA-680632, SNS-314, TAK-901, VX-680 (MK-0457, tozasertib), and ZM-447439.

Myosin Light Chain Kinase Inhibitors. Myosin light chain kinase (MLCK) is involved in late stages of myosin stimulation; it acts through MLC and is responsible for stress fibers activation and lamellipodia formation. Exemplary MLCK inhibitors include, but are not limited to, A3 HCl, Gö 7874 HCl, InSolution™ K-252a (*Nocardiopsis* sp.), K-252a (*Nocardiopsis* sp.), K-252b (*Nocardiopsis* sp.), ML-7 HCl, ML-9 HCl, MLCK inhibitor peptide 18, piceatannol, and staurosporine (*Streptomyces* sp.).

Phorbol 12-myristate 13-acetate (PMA). Protein kinase C (PKC) is involved in megakaryocyte differentiation and growth and its activation through PMA increases cell ploidy.

Blebbistatin. Blebbistatin inhibits myosin II and consequently the last steps of cytokinesis and cell division, thus allowing the cell to undergo polyploidization and increase the nuclear material.

Stathmin inhibitor (staurosporine). Stathmin is involved in microtubule formation and the final steps of cytokinesis. Its inhibition blocks cell division and increases megakaryocyte ploidy.

Increased oxygen concentration during culture increases megakaryocyte polyploidization.

As the megakaryocyte matures, its surface receptors change, making it less adhesive to the bone marrow niche, but ready for residence near the blood vessels in the perivascular niche. Once the megakaryocyte is mature it is lured out of the bone marrow niche toward the perivascular niche by signals from the vascular niche, such as SDF-1α. Importantly, as it leaves the bone marrow niche, the megakaryocyte is freed from the inhibition of platelet formation. Near the blood vessels, the megakaryocyte also encounters extracellular proteins that signal the cell to make platelets. Platelet formation is initiated by the extrusion of very long cytoplasmic processes called proplatelets, which contain all of the platelet elements. These processes extend through the blood vessel walls into the blood stream and are released by the shear forces of the flowing blood.

Rho/Rock pathway inhibitors increase proplatelet formation in cultured megakaryocytes. The mechanism involves reversal of the bone marrow niche-induced inhibition of proplatelet formation. Inducing megakaryocyte apoptosis with nitric oxide (such as, but not limited to, S-nitrosoglutathione) and/or caspase activators (such as, but not limited to, Fas-ligand) also increases megakaryocyte proplatelet formation and platelet release. PKC activation with PMA induces megakaryocyte differentiation and consequently increases proplatelet formation. Rac1 activation, CDC42 activation, hirudin and c-Myc inhibition also increase proplatelet formation.

A constant flow of nutrient-rich medium is important in the process of increasing proplatelet formation and platelet release and is applied with a pump to the megakaryocyte culture in a flow rate range between about 100 μl/min and about 55,000 μl/min. In number of possible pump designs could be used, such as syringe pumps, peristaltic pumps, etc. In some embodiments, the flow rate is in a range of about 200 μl/min to about 400 μl/min, about 150 μl/min to about 350 μl/min, about 250 μl/min to about 350 μl/min, about 250 μl/min to about 450 μl/min, or about 100 μl/min to about 400 μl/min. In some embodiments, the flow rate is in a range of about 15,000 μl/min to about 55,000 μl/min, about 20,000 μl/min to about 50,000 μl/min, about 25,000 μl/min to about 45,000 μl/min, or about 30,000 μl/min to about 35,000 μl/min. Platelets are collected after release in a specific platelet bag with preservative solutions. Produced megakaryocytes and platelets are analyzed for antigen expression (CD41, CD42b, CD61), activation (P-selectin). Then they may be cultured for contamination, CFU-MEG grown assay, and flow analysis of ploidy.

Disclosed herein are methods and systems for producing platelets in artificial systems in which megakaryocyte progenitor cells are grown and matured in experimental matrices containing proteins found in the bone marrow niche environment. The creation of defined physical and chemical environments drives megakaryocyte maturation and subsequent platelet formation. The defined environments are designed into self-contained modules that are used sequentially in a bioreactor to efficiently generate platelets from stem cells.

The term “megakaryocyte progenitor cells,” as used herein, refers to hematopoietic stem cells committed to at least the megakaryocyte lineage and includes, but is not limited to, cells in the umbilical cord blood, bone marrow, and peripheral blood as well as hematopoietic stem cells, human embryonic stem cells, and induced pluripotent stem cells.

In one embodiment, a platelet production device is used to increase the cell expansion of stem cells and/or megakaryocyte progenitors. A schematic of an exemplary platelet production device for producing platelets in vitro can be found in FIG. 1. The bioreactors, vessels, chambers, reservoirs, niches, and bags of the platelet production device are connected by a series of sterile tubing which may optionally contain pumps, valves, membranes, filters, and sensors as appropriate.

The platelet production device 100 comprises a bioreactor 102 into which a source of stem cells is placed. The stem cells are megakaryocyte-producing progenitor cells including, but are not limited to, hematopoietic stem cells (from umbilical cord blood, bone marrow, and/or peripheral blood), embryonic stem cell lines, induced pluripotent stem cells, and fibroblasts. The progenitor cells are optionally enriched for CD34+ cells prior to placement in the bioreactor 102. The bioreactor 102 further contains a suitable first growth medium including appropriate growth factors.

After a culture period of between about 1 week and about 1 month, the expanded progenitor cells are transferred from bioreactor 102 into a maturation chamber 110 for maturation into large, polyploidy megakaryocytes. In alternative embodiments, the culture period is between about 2 weeks and about 1 month, about 3 weeks and about 1 month, between about 2 weeks and about 3 weeks, or between about 1 week and about 3 weeks. Maturation chamber 110 comprises an artificial bone marrow niche environment which comprises a cell growth matrix such as, but not limited to, MATRIGEL®, gelatin, fibrinogen, collagen, methylcellulose, or extracellular matrix gel. MATRIGEL® is a gelatinous protein mixture secreted by Engelbreth-Holm-Swarm (EHS) mouse sarcoma cells and mimics the complex extracellular environment found in many tissues. This environment also contains all the factors necessary for maturation and polyploidization of the megakaryocytes including a plurality of factors selected from the group consisting of nicotinamide (vitamin B3), folic acid, vitamin B12, Rho/Rock inhibitors, Src inhibitors, stathmin inhibitors, Aurora-B inhibitors, Bcr-Abl inhibitors, induction of cyclin D1, D3 and p19, phorbol 12-myristate 13-acetate (PMA), blebbistatin, Rac1 inhibitors, CDC42 inhibitors, and MLCK inhibitors. The culture environment in maturation chamber 110 is also adapted to have an increased oxygen concentration compared to standard cell culture conditions. The increased oxygen concentration is between 10% and 30% $PO_2$. In alternative embodiments, the $PO_2$ is between about 15% and about 25%; in another embodiment, the $PO_2$ is between about 17% and about 22%; and in another embodiment the $PO_2$ is about 20%. The expanded megakaryocyte progenitor cells are maintained in maturation chamber 110 for a period of time, such as a period of time between about 2 days and 12 days of culture, until a population of mature and polyploid megakaryocytes is obtained. In alternative embodiments, the culture period is between about 3 days and about 11 days, between about 4 days and about 10 days, between about 5 days and about 11 days, between about 6 days and about 11 days, between about 7 days and about 11 days, between about 8 days and about 11 days, between about 5 days and about 9 days, or between about 6 days and about 8 days.

Mature and polyploid megakaryocytes are then transferred to cell separation chamber 120 which contains a concentration gradient of bovine serum albumin (BSA) 124. The concentration gradient of BSA separates the megakaryocytes according to their size. Thus, large, mature polyploid megakaryocytes 126 are concentrated in the bottom of the chamber and the small, immature megakaryocytes 122 are at the surface. The mature megakaryocytes are then transferred to the platelet production module 135, and the immature megakaryocytes are passaged through recirculating loop 140 back to the maturation chamber 110 for further maturation.

The mature megakaryocytes are passed into platelet production chamber 135, which is comprised of a series of platelet release chambers 130, each platelet release chamber 130 containing a 3D matrix, membrane, or scaffold 150 with pores between about 2 μm and about 6 μm and coated with factors that stimulate proplatelet formation and platelet release. Platelet production chamber 135 may also comprise a single platelet release chamber 130. In alternative embodiments, the 3D matrix comprises pores between about 1 μm and about 6 μm, and between about 2 μm and about 5 μm. In some embodiments, the 3D matrix or membrane is less than about 400 μm thick, less than about 300 μm thick, or even less than about 200 μm thick. In some embodiments, the 3D matrix or membrane is at least about 50 μm thick, at least about 100 μm thick, or even at least about 150 μm thick. In some embodiments, the 3D matrix or membrane is between about 100 μm and about 200 μm in thickness.

Suitable membranes include those that are spun, woven, extruded, vacuum-formed, or 3D-printed. Exemplary matrices include, but are not limited to, gelatin, MATRIGEL®, ALGIMATRIX®, alginate, polypropylene, styrene, polystyrene, and polyester in the form of beads, mesh, felt or other 3D structures coated with a plurality of growth factors including, but not limited to, fibrinogen, fibronectin, von Willebrand factor (vWF), Fas-ligand, PMA, nitric oxide, Rho/Rock inhibitors, Src inhibitors, Rac1 inhibitors, CDC42 inhibitors, SDF-1α, hirudin, heparin, c-Myc inhibitors, MLCK inhibitors, and Rho/Rock inhibitors. In some embodiments, the 3D matrix or membrane is charged or coated such as with ECM protein.

Platelet production chamber 135 also includes a reservoir 138 containing a third growth medium. Each of the platelet release chambers 130 are attached to a syringe pump 160 that provides flow and shear stress to the proplatelet formation environment. The platelet release chambers are additionally connected to syringe pump 170 and reservoir 175 which provides tangential flow (shear stress) for releasing and collecting platelets. Released platelets are collected and stored in platelet collection chamber 180. The flow and shear stress may be provided by the same fluid sources or by different fluid sources.

Figure 7:
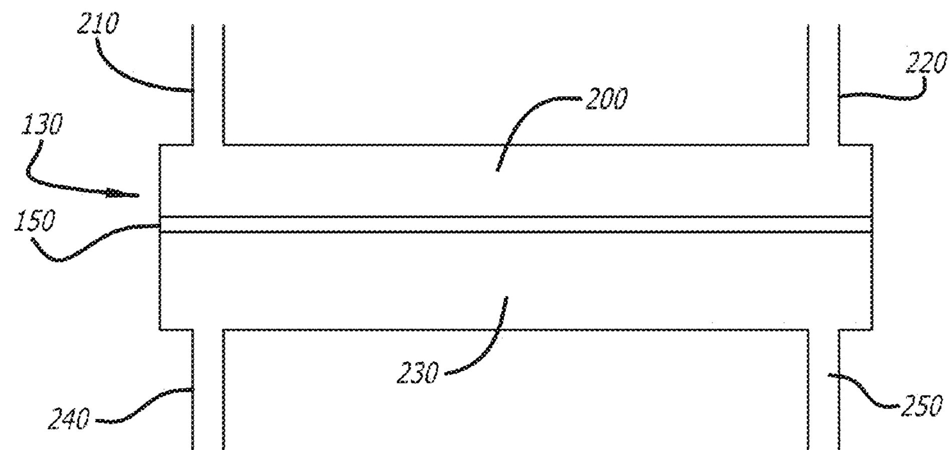
FIG. 7 is an illustration of one embodiment of a platelet release chamber according to the present disclosure.

According to some embodiments, platelet release chamber 130 comprises a top plate and a bottom plate with scaffold 150 comprising a membrane sandwiched between the top and bottom plates. These combined elements comprise one embodiment of platelet release chamber 130. FIG. 7 illustrates one exemplary configuration having a top plate 200 and a bottom plate 230. Top plate 200 includes fluid inlet 210 and fluid outlet 220. Top plate 200 is configured to allow for mature megakaryocytes to enter fluid inlet 210 and lodge or adhere to the surface of scaffold 150. A fluid, such as the third growth medium, may then be passed through the top plate (e.g., via fluid inlet 210 and fluid outlet 220). In some embodiments, at least some of a fluid passing through top plate 200 passes through scaffold 150 into bottom plate 230. In some embodiments, the fluid—whether or not any passes through to bottom plate 230—applies a force to the mature megakaryocytes that holds the megakaryocytes against or within scaffold 150. This may allow or cause the megakaryocytes to extend their proplatelet processes through the pores or matrix of scaffold 150.

In some embodiments, top plate 200 and bottom plate 230 are configured and/or fluid flow through top plate 200 and bottom plate 230 is controlled so as to reduce or eliminate the shear stress experienced by the mature megakaryocytes. In such embodiments the proplatelet processes extending through the pores or matrix of scaffold 150 experience most or all of the shear stress created in chamber 135.

In some embodiments the shear rate of the fluid flowing through top plate 200 is approximately the same as the shear rate of the fluid flowing through bottom plate 230. In some embodiments, the ratio of the shear rate of the fluid in top plate 200 to the shear rate of the fluid in bottom plate 230 is less than about 1:2, less than about 1:3, less than about 1:4, less than about 1:5, less than about 1:10, or even less than about 1:100. In some embodiments, the flow rate of the fluid in the respective plates is approximately equal, but the shear rates achieved in the respective plates differs by virtue of differently design and/or sized channels in the respective plates. For example, in some embodiments, a higher shear rate is achieved by using smaller channels in bottom plate 230 than are used in top plate 200 even though the flow rate of the fluid through the two plates may be similar.

FIG. 7 illustrates platelet release chamber 130 comprising a top and a bottom portion that are separate units; however, it is contemplated that the same could easily be achieved with unitary construction. In some embodiments, scaffold 150 could be simply inserted into a chamber of unitary construction. In some embodiments, scaffold 150 may itself comprise a part of the chamber. In other words, the materials and methods used to form platelet release chamber 130 could also be used to form scaffold 150. However, in some embodiments, a removable, replaceable scaffold may be desirable.

In some embodiments, a cap is placed over fluid outlet 220 that completely or at least partially prevents fluid from passing through fluid outlet 220. In such configurations, the fluid, or third growth medium, is then more likely to pass through scaffold 150 so as to apply pressure on the megakaryocytes so as to keep them against scaffold 150 and to direct the proplatelet processes through scaffold 150 and into bottom plate 230.

Bottom plate 220, similar to top plate 200, may include a fluid inlet 240 and a fluid outlet 250. A fluid, such as the third growth medium, is brought into bottom plate 230 through fluid inlet 240. The fluid then interacts with scaffold 150 so as to remove at least some platelets from the proplatelet processes extending from the mature megakaryocytes. The fluid then flows out of bottom plate 230 by way of fluid outlet 250. In some embodiments, the use of cap or flow reduction device located at fluid outlet 220 insures that the fluid will not generally flow through scaffold 150 from bottom plate 230 to top plate 200.

Figure 8:
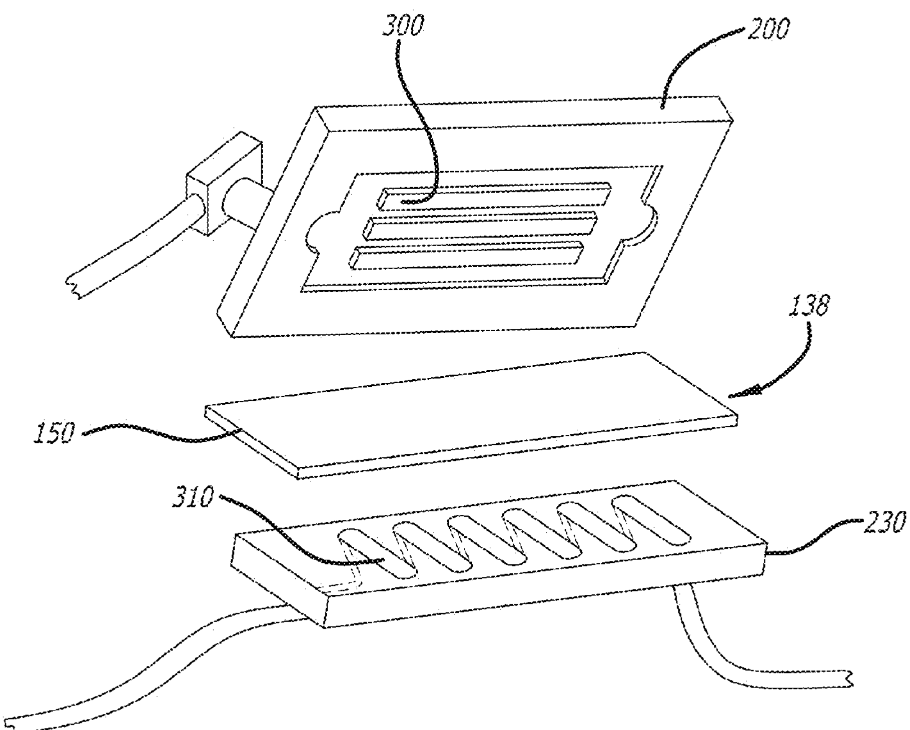
FIG. 8 is a perspective view of one embodiment of a platelet release chamber according to the present disclosure.

Referring to FIG. 8, it can be seen that platelet release chamber 130 may include one or more top channels 300 in top plate 200. Top channels 300 may be configured in any suitable manner. In some embodiments, channels are used rather than simply a void space so that the edges of the channels may secure scaffold 150 in place between top plate 200 and bottom plate 230.

Similar to top channels 300 of top plate 200, bottom plate 230 may also include one or more bottom channels 310. Again, the use of channels rather than simply void spaces may help secure scaffold 150 between top plate 200 and bottom plate 230. Bottom channels 310 may be configured in any suitable manner. In some embodiments, it is desirable to control and direct the flow of a fluid, such as the third growth media, through bottom plate 230 so as to achieve uniform fluid flow and a controlled and predictable shear force at the interface of scaffold 150.

As explained above, the shear force (i.e., shear stress or shear rate) achieved in the platelet release chambers 138 depends in part on the flow rate of the third growth medium. One of skill in the art will understand that the actual shear force achieved in platelet release chambers 138 will also be a function of the area of the platelet release chambers 138 or, more specifically, the surface area of scaffold 150 exposed to the volume within platelet release chambers 138 or the cross-sectional area through which the fluid flows. Thus, the same shear force could be achieved with greater volumetric flow rates if the surface area increases accordingly. Similarly, the same shear force could be achieved with lower volumetric flow rates if the surface area decreases accordingly.

According to some embodiments, the surface area of scaffold 150 is approximately equal to, and coextensive with, at least one interior surface of platelet release chamber 138. In some embodiments, the surface area of scaffold 150 is not coextensive. In some embodiments, the surface area of scaffold 150 is less than the area of one side of the interior surface of platelet release chamber 138.

In some embodiments, a flow path is established for the third growth medium. The flow path may comprise one or more channels where each channel allows the third growth medium to flow along the surface of scaffold 150. In some embodiments, the flow rate—which may be defined as either the flow rate of a fluid through either top plate 200, through bottom plate 230, or the flow rate through both top plate 200 and bottom plate 230 combined—may be from about 100 μl/min to about 55,000 μl/min. In some embodiments, a desirable shear force is achieved using a flow rate of about 15,000 μl/min to about 50,000 μl/min. Again, the shear force also depends on the shape and size of the flow path. Accordingly, although a flow rate of about 15,000 to about 50,000 μl/min has been found desirable in some embodiments, a faster or slower flow rate would also be desirable depending on any changes to the area of scaffold 150 or the configuration of bottom channels 310.

In some embodiments, the flow rate, defined as the flow rate of fluid through both top plate 200 and bottom plate 230 is from about 400 μL/min to about 600 μL/min. The independent flow rate through either top plate 200 or bottom plate 230 will depend on the selected configuration. In some embodiments, the flow rate is the same through either plate, though the rates may also vary. In some embodiments, the flow through top plate 200 is sufficient to achieve a positive pressure against scaffold 150.

In some embodiments, the shape of bottom channels 310 is rectangular, square, ovoid, or circular. In some embodiments, one or both top channels 300 and bottom channels 310 comprise a rectangular shape having a width of about 1 mm to about 20 mm, a depth of between about 0.1 mm and about 10 mm, and a length of between about 10 mm to about 100 cm. In some embodiments, top channels 300 have a width of about 2 mm, a depth of about 1.5 mm, and a length of about 40 mm. In some embodiments, bottom channels 310 have a width of about 4 mm, a depth of about 0.5 mm, and a length of about 20 mm. According to some embodiments, one or both of top channels 300 and bottom channels 310 exhibit a circular or semi-circular cross-sectional area.

The method used to calculate the shear rate in both the top channels 300 and the bottom channels 310 will depend on the shape of those channels. Generally, different shaped channels requires the use of different equations; however, in some instances an equation for one type of channel can be used to approximate the shear rate in a different type of channel. In some instances, slightly modifying an equation yields a reasonably accurate approximation.

Assuming that the shear rate achieved in rectangular channels can be roughly approximated using the shear rate formula for circular channels of the same size, the shear rate can be calculated using the formula:

$$\dot{\gamma} = \frac{4 \cdot Q}{\pi \cdot r^3}$$

According to at least one embodiment having rectangular channels, r is approximated as half the width of the channel. In other words, where the channel width is about 0.5 cm, r is approximated as 0.25 cm. In some embodiments, the volumetric flow rate is about 20,000 μl/min or 0.3333 ml/s. Thus, $$\dot{\gamma} = \frac{4 \cdot 0.3333 \text{ ml/s}}{\pi \cdot (0.25 \text{ cm})^3}$$

$$\dot{\gamma} = 27.16 \text{ s}^{-1}$$

According to some embodiments, the shear rate ranges from about 1 $s^{-1}$ to about 100 $s^{-1}$, from about 1 $s^{-1}$ to about 50 $s^{-1}$, from about 20 $s^{-1}$ to about 80 $s^{-1}$, about 30 $s^{-1}$ to about 70 $s^{-1}$, from about 4 $s^{-1}$ to about 8 $s^{-1}$.

Table 1 below illustrates the relationship between volumetric flow rate and the approximate radius of a channel next to scaffold 150.

TABLE 1

Exemplary shear rates ($s^{-1}$) based on flow rate and radius

| | | Approximate radius (cm) | | | | | |
|---|---|---|---|---|---|---|---|
| | | 0.15 | 0.2 | 0.25 | 0.3 | 0.35 | 0.4 |
| Flow rate (ml/min) | 15 | 94.31404 | 39.78873577 | 20.37183 | 11.78926 | 7.424137 | 4.973592 |
| | 20 | 125.7521 | 53.0516477 | 27.16244 | 15.71901 | 9.89885 | 6.631456 |
| | 25 | 157.1901 | 66.31455962 | 33.95305 | 19.64876 | 12.37356 | 8.28932 |
| | 30 | 188.6281 | 79.57747155 | 40.74367 | 23.57851 | 14.84827 | 9.947184 |
| | 35 | 220.0661 | 92.84038347 | 47.53428 | 27.50826 | 17.32299 | 11.60505 |
| | 40 | 251.5041 | 106.1032954 | 54.32489 | 31.43801 | 19.7977 | 13.26291 |
| | 45 | 282.9421 | 119.3662073 | 61.1155 | 35.36777 | 22.27241 | 14.92078 |
| | 50 | 314.3801 | 132.6291192 | 67.90611 | 39.29752 | 24.74712 | 16.57864 |
| | 55 | 345.8181 | 145.8920312 | 74.69672 | 43.22727 | 27.22184 | 18.2365 |

Younggon Son has put forth an alternative equation for approximating shear rate in rectangular channels. Younggon Son, *Determination of shear viscosity and shear rate from pressure drop and flow rate relationship in a rectangular channel,* 48 Polymer 632 (2007). According to Son, the apparent shear rate of a rectangular die is $$\dot{\gamma} = \left(\frac{6Q}{WH^2}\right)\left(1 + \frac{H}{W}\right)f^*\left(\frac{H}{W}\right)$$

where W is width of the rectangular channel, H is the height of the rectangular channel, and function $f^*$ is calculated using data provided by Son.

Using Son's apparent shear rate equation as well as Son's calculated values for $f^*$, sample shear rates are shown in Table 2 below, which illustrates the relationship between volumetric flow rate and the ratio between the height and the width of a rectangular channel. For the sake of simplicity, the channel has been assumed to have a constant height of about 5 mm. Accordingly, the only variables that have been adjusted are the channel width and the flow rate.

TABLE 2

Exemplary shear rates ($s^{-1}$) for a rectangular channel

| | | H/W ratio | | | | | | |
|---|---|---|---|---|---|---|---|---|
| | | 0.125 | 0.25 | 0.375 | 0.5 | 0.625 | 0.75 | 0.875 |
| Flow rate (ml/min) | 0.1 | 1.205963 | 4.74553 | 10.7106 | 19.43892 | 31.4698 | 47.50346 | 68.35244 |
| | 0.15 | 1.808944 | 7.118295 | 16.0659 | 29.15838 | 47.2047 | 71.25519 | 102.5287 |
| | 0.2 | 2.411925 | 9.49106 | 21.4212 | 38.87784 | 62.9396 | 95.00693 | 136.7049 |
| | 0.25 | 3.014906 | 11.86382 | 26.7765 | 48.5973 | 78.6745 | 118.7587 | 170.8811 |
| | 0.3 | 3.617888 | 14.23659 | 32.1318 | 58.31677 | 94.4094 | 142.5104 | 205.0573 |
| | 0.35 | 4.220869 | 16.60935 | 37.48711 | 68.03623 | 110.1443 | 166.2621 | 239.2336 |
| | 0.4 | 4.823850 | 18.98212 | 42.84241 | 77.75569 | 125.8792 | 190.0139 | 273.4098 |
| | 0.45 | 5.426831 | 21.35488 | 48.19771 | 87.47515 | 141.6141 | 213.7656 | 307.5860 |
| | 0.5 | 6.029813 | 23.72765 | 53.55301 | 97.19461 | 157.3490 | 237.5173 | 341.7622 |
| | 0.55 | 6.632794 | 26.10041 | 58.90831 | 106.9141 | 173.0839 | 261.2690 | 375.9384 |
| | 0.6 | 7.235775 | 28.47318 | 64.26361 | 116.6335 | 188.8188 | 285.0208 | 410.1147 |

According to some embodiments where the measurable volumetric flow rate is the total rate of flow both through top plate 200 and bottom plate 230, the actual flow rate through bottom plate 230 will be fraction of the total flow. In some embodiments, the flow rate through bottom plate 230 is less than 100% of the total flow rate through platelet release chamber 138. In some embodiments, the flow rate through bottom plate 230 is less than 95%, less than 90%, less than 85%, less than 80%, less than 75%, or even less than 50% of the total flow rate through platelet release chamber 138. In some embodiments, the flow rate through bottom plate 230 is greater than 50%, greater than 60%, greater than 70%, greater than 80%, or even greater than 90% of the total flow rate through platelet release chamber 138.

In some embodiments, it may be desirable to expand the size of platelet release chamber 138 as well as the exposed surface of scaffold 150. Enlarging the configuration may allow for an increased rate of platelet growth and collection. However, the same shear rate may be desired and may be achieved using a greater volumetric flow rate. Additionally, it may also be possible to achieve the same shear rate with a larger surface area by maintaining channels of the same size but by multiplying the number of channels.

In one embodiment, the bioreactors, vessels, chambers, and bags are cell collection bags, such as sterile blood collection bags known to persons of ordinary skill in the blood banking arts. In other embodiments, the vessels, chambers, and bags are sterile biocompatible containers of any design.

In some embodiments, the bioreactors, vessels, chambers, and bags are comprised of one or more plastics, one or more metals, one or more polymers, and/or glass. Some embodiments are manufactured using polypropylene and/or polystyrene. One of skill in the art will recognize that other materials will be substantially equivalent to those disclosed here.

Also disclosed herein is a method for the production of platelets in an artificial in vitro system.

The method comprises (1) culturing the stem cells under conditions to expand the population of megakaryocyte progenitor cells; (2) differentiating and maturing the megakaryocyte progenitor cells into mature megakaryocytes; (3) isolating the mature megakaryocytes; (4) producing platelets from the mature megakaryocytes; and (5) collecting the platelets.

For the culture and expansion step, the megakaryocyte progenitor cells are cultured under conditions which include a first growth medium, and appropriate oxygen and pH levels. In particular, a higher pa concentration and pH than standard cell culture conditions are necessary for appropriate megakaryocyte yield. Suitable $PO_2$ concentrations are in the range of about 10% and about 30% $PO_2$, and suitable pH is in the range of about 7.2 and about 7.6. In alternative embodiments, the $PO_2$ is between about 15% and about 25%; in another embodiment, the $PO_2$ is between about 17% and about 22%; and in another embodiment the $PO_2$ is about 20%. In alternative embodiments, the pH is between about 7.3 and about 7.5, or between about 7.2 and about 7.4. In another embodiment, the pH is about 7.4. The first growth media includes a plurality of growth factors selected from the group consisting of aryl-hydrocarbon inhibitor/stem regenin-1, notch-ligand delta-1, prostaglandin-E2, SALL4 gene activators, histone acetyltransferase inhibitor, Hoxb4 activators, SDF-1$\alpha$, valproic acid, p38 inhibitors, co-culture with mesenchymal stem cells and/or OP-9 cells, tropoelastin, copper chelation, Z-VAD-FMK, banana lectin, garlic lectin, interferon-$\alpha$, TPO, SCF, IL-3, IL-6, IL-11, and FLT-3L. In one embodiment, the culture and expansion step is performed in a culture vessel, for example, the bioreactor 102 of FIG. 1.

Optionally the megakaryocyte progenitor cells are enriched for CD34+ cells prior to expansion. Methods for enrichment of CD34+ cells are known to persons of ordinary skill in the art. One exemplary method of enrichment of CD34+ cells is using a negative selection method. An exemplary negative selection method is a rapid cell separation method to isolate highly purified cells directly from mixed cell populations including blood. An exemplary method uses ROSETTESEP® technology (Stem Cell Technologies) which comprises tetrameric antibody complexes which aggregate unwanted cells with red blood cells present in the sample, forming immunorosettes, which are removed by density centrifugation. The desired cells are not labeled with antibody and are immediately ready for culture.

In one embodiment, the stem cell expansion and culture step is conducted for about 15 to about 30 days. In alternative embodiments, the stem cell expansion and culture step is conducted for about 15 to about 25 days, about 20 to about 30 days, about 17 to about 28 days, about 19 to about 26 days, about 21 to about 24 days, or about 22 to about 28 days.

The expanded megakaryocyte progenitor cells are then cultured under conditions to differentiate and mature the progenitors into mature megakaryocytes. These conditions mimic the bone marrow niche environment in which megakaryocytes mature in vivo and the artificial bone marrow niche environment includes both a cell growth matrix and a second growth medium containing a plurality of growth factors. Exemplary cell growth matrices include, but are not limited to, MATRIGEL®, gelatin, fibrinogen, collagen, methylcellulose, and extracellular matrix gel. The plurality of growth factors is selected from the group consisting of serotonin, arachidonic acid, Z-VAD-FMK, TPO, SCF, IL-3, IL-6, FLT-3L, nicotinamide (vitamin B3), folic acid, vitamin B12, Rho/Rock inhibitors, Src inhibitors, Aurora-B inhibitors, Bcr-Abl inhibitors, induction of cyclins D1, D3 and p19, PMA, blebbistatin, and MLCK (Myosin light chain kinase inhibitor peptide 18) inhibitors. In one embodiment, the differentiating and maturing step is performed in the maturation chamber 110 of FIG. 1.

In another embodiment, the artificial bone marrow niche environment further includes mesenchymal stem cells. An exemplary source of mesenchymal stem cells is bone marrow. The mesenchymal stem cells can be mixed with the megakaryocyte progenitor cells or segregated from the megakaryocyte progenitor cells by a porous membrane which allows the passage of cellular materials (but not whole cells) from the mesenchymal stem cells to the megakaryocyte progenitor cells.

In one embodiment, the differentiation and maturation step is conducted for about 8 to about 11 days. In alternative embodiments, the differentiation and maturation step is conducted for about 9 to about 10 days, from about 8 to 10 days, or about 9 to 11 days.

The mature megakaryocytes are isolated on a density gradient before entering the platelet production phase. Mature megakaryocytes enter the platelet production phase, and immature megakaryocytes are returned to the artificial bone marrow niche for further maturation.

The mature megakaryocytes are then cultured under conditions which induce the production of platelets. The megakaryocytes are transferred to chambers in which a filter or membrane is present on one surface to allow the free flow of a third growth medium from a reservoir, retaining megakaryocytes, and allowing platelets to pass through. The third growth medium may comprise culture media, Hepes buffered modified Tyrodes (HBMT) or other buffer, PBS, and/or PAS. In some embodiments, the third growth medium further contains a plurality of growth factors selected from, fibrinogen, fibronectin, vWF, Fas-ligand, PMA, nitric oxide, Rho/Rock inhibitors, Src inhibitors, MLCK inhibitors, hirudin, heparin, c-Myc inhibitors and SDF-1$\alpha$. In some embodiments, the third growth medium also includes at least one of the following additives: cytokines, nutrients, and antibiotics. In some embodiments, no additives are used. In one embodiment, the platelet production step is conducted in platelet production chamber 135 of FIG. 1.

In one embodiment, the proplatelet formation and platelet collection step is conducted for about 1 to about 2 days.

The platelets produced are then collected in a suitable vessel for further use. In one embodiment, the vessel is platelet bag 180 of FIG. 1.

The platelets produced by the system and method disclosed herein are suitable for use in a variety of diseases and conditions including, treatment of thrombocytopenia, treatment of infection, support during surgery, treatment of platelet defects, treatment of bleeding conditions, and others.

EXAMPLES

Example 1

Isolation and Culture of Stem Cells

Platelets can be derived from different sources of stem cells. Described herein are methods for selecting and growing stem cells from different sources.

Human Embryonic Stem Cells. HeSC are derived from cell lines including, but not limited to, H1, H7, H9, HuES-3, MA01, MA40 and MA09. The HeSC are differentiated into hemangioblasts/blasts cells with the addition to serum-free medium of bone morphogenic protein 4 (BMP-4), vascular endothelial growth factor (165aa, VEGF165), stem cell factor (SCF), thrombopoietin (TPO) and FLT-3 ligand (FLT-3L). The cultured hemangioblasts can be co-cultured with mesenchymal stem cells (MSC) and are finally differentiated into megakaryocytes with cytokines such as TPO, SCF, IL-6, IL-9, IL-11, VEGF, and fibroblast growth factor (FGF).

Induced pluripotent stem cells. IPSC are derived from somatic and mature cells and transfected with genes that code transcriptional factors known to maintain pluripotency including, but not limited to, Oct3/4, Sox2, Nanog, Lin28, c-Myc, and Klf-4. The transformation of mature cells into hematopoietic progenitors is also possible using just one gene modification (Oct4). Gene transfection is performed using virus (adenovirus, lentivirus) and/or plasmids. The immature and pluripotent cells are then co-cultured with MSC and cytokines such as TPO, SCF, IL-3, and IL-9 in medium to differentiate the IPSC into hematopoietic progenitors and megakaryocytes.

Hematopoietic Stem Cells. Hematopoietic stem cells are collected from the bone marrow, from peripheral blood with an apheresis machine, or from umbilical cord blood (UCB).

UCB is collected from the umbilical cord vein right after delivery. Approximately 100 ml are collected, stored with anticoagulant (CPD-A), and used within 24 hours. Total leukocytes are separated from red blood cells by sedimentation with dextran. The lymphocytes are separated from the total leukocytes by density separation with Ficoll. Stem cells, which are identified by the CD34+ surface protein, are isolated using anti-CD34+ antibodies linked to metal beads, which bind to the stem cells and are retrieved with a magnet. Hematopoietic stem cells can also be selected with a second negative selection method. The negative selection method involves using ROSETTESEP® (Stem Cell Technologies) during the preparation and has a lower final CD34+ purity (around 10%). Thus, this method allows the cells to grow surrounded by other hematopoietic cells, in an environment closer to the bone marrow niche.

The CD34+ cells are then cultured in the presence of one or more factors selected from the group consisting of TPO, SCF, IL-11, IL-6, and IL-3 for expanding and differentiating the stem cells toward megakaryocytopoiesis.

Fibroblasts. Fibroblasts can be directly differentiated into hematopoietic stem cells by activating specific gene of immaturity. Mature fibroblasts can be transduced with genes, for example, Oct-4, allowing them to express characteristics of hematopoietic progenitors and, therefore, be differentiated into megakaryocytes and platelets.

Hematopoietic stem cells are laboratory expanded to increase the number of progenitors and consequently increase the platelet production. Four different matrices are evaluated for support of megakaryocytopoiesis including 1) gelatin; 2) MATRIGEL®, a mixture of extracellular matrix proteins derived from cellular basement membranes; 3) methylcellulose, a gelatin-like liquid used in stem cell culture; and 4) polyester mesh scaffolding, which is a surgical grade membrane that has been used for stem cell culture. Different concentrations of methylcellulose, MATRIGEL®, or gelatin are used. These are mixed with the cytokines described above, as well as different concentrations of collagen I. The polyester mesh can be incubated with different concentrations of soluble collagen I. In alternative embodiments, cells are culture expanded prior to culture in the matrix.

In another embodiment, the megakaryocytes are cultured in association with mesenchymal stem cells, also derived from UCB. These mesenchymal stem cells can differentiate into bone and cartilage. They have recently been described as a means of mimicking the microenvironment of the bone marrow niche. In another embodiment, the megakaryocyte growth is maximized on the bone marrow cells, and then the megakaryocytes are transitioned to growth on only the secreted matrix of the bone marrow cells. The bone marrow cells are grown on culture dishes and then the cells are removed, leaving behind the secreted proteins. Cord blood-derived CD34+ stem cells or megakaryocytes are then placed directly onto a plate that is coated with a layer of bone marrow stroma cells in the presence of cytokines. The growing megakaryocytes are evaluated daily to characterize their size, shape, nucleus, and differentiation capacity.

Example 2

Effect of CD34+ Negative Selection on Megakaryocyte Expansion

Umbilical cord blood was obtained and the CD34+ cells were selected by negative selection (ROSETTESEP®) or positive selection. The positive selection method is based on the separation of stem cells using beads and magnetic columns. Beads attach to specific stem cell surface markers and are positively selected with the magnetic columns.

Figure 4A:
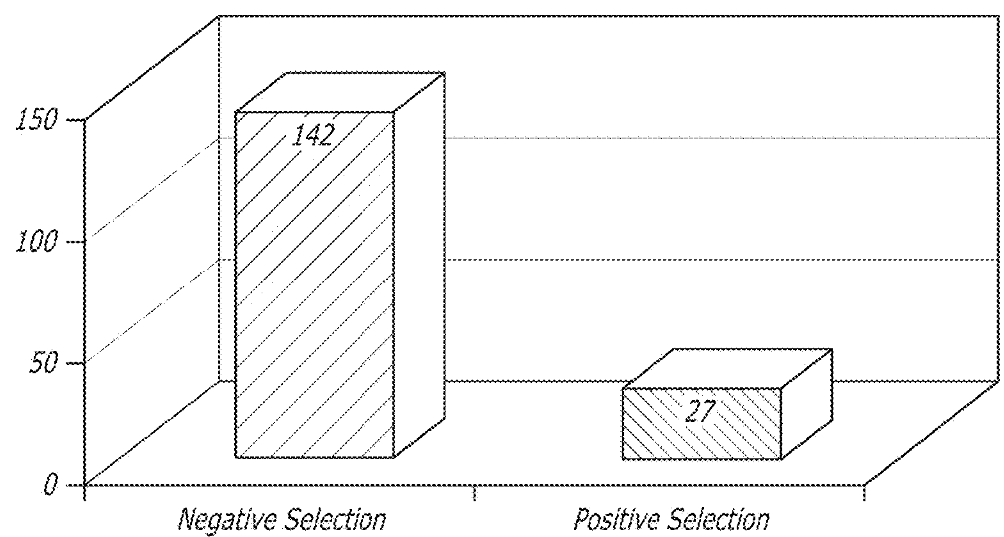
FIGS. 4A and B depict the fold expansion (FIG. 4A) and surface antigen expression (FIG. 4B) of megakaryocytes expanded from negatively selected CD34+ umbilical cord blood. The positive selection bar in FIG. 4A is a historical control.
Figure 4B:
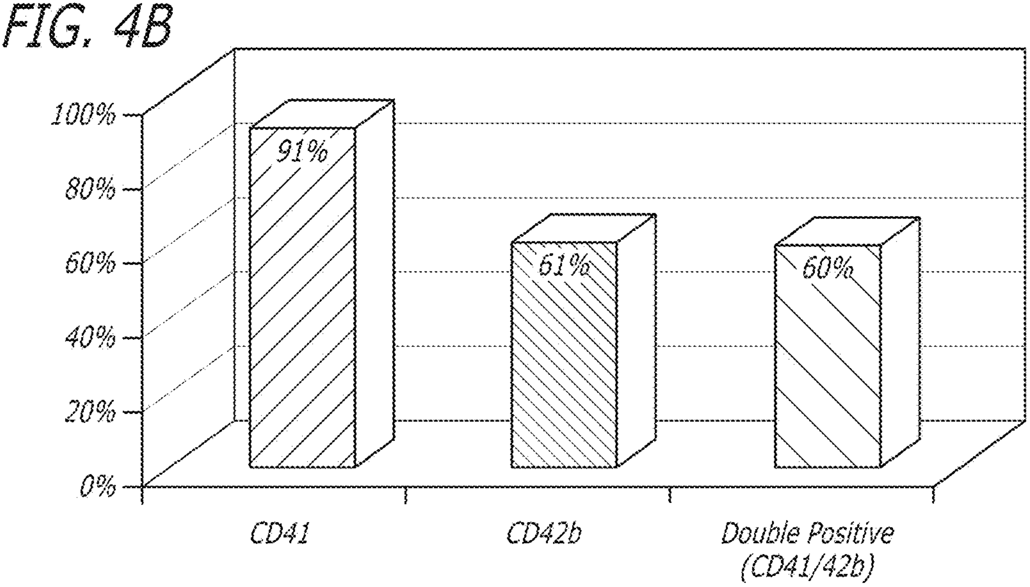

After negative selection, $1\times10^5$ total nucleated cells (TNC) and $7\times10^3$ CD34+ cells were plated in 24 well plates at a concentration of $2\times10^5$ cells/ml (FIG. 2). STEMSPAN® medium (Stem Cell Technologies) was used for culture with added thrombopoietin (50 ng/ml) and stem cell factor (50 ng/ml) as cytokines. Fresh medium was added to the culture every 3 days, and the cells were replated on day 5 of culture. The culture was carried out at 37° C. with 5% $CO_2$ and ambient oxygen. The cultured cells are depicted in FIGS. 3 and 4. The cells were analyzed by flow cytometry on day 11 of culture for CD41 and CD42b antigen expression as well as for ploidy. A BD Canto flow machine was used for analysis. The positive selection results for comparison were selected from the literature.

The culture was started with $7\times10^3$ CD34+ cells, and the final yield of megakaryocytes was $1\times10^6$ cells with a fold expansion of 142. The antigen expression analysis of the megakaryocytes demonstrated that CD41 and CD42b were expressed on 91% and 61% of the cells, respectively, and 60% of the cells were double positive (CD41/CD42b). The ploidy analysis showed that 65% of the megakaryocytes were 2N, 20% were 4N, and 15% were above 4N.

According to the literature, the CD34+ expression in the positive selected cell population should be over 90%, and the fold expansion with different protocols for megakaryocytes was from 4 to 27 fold.

The negative selection technique allows the CD34+ stem cells to grow under the influence of other hematopoietic cells and provides a better expansion microenvironment. The high megakaryocyte fold-expansion (142-fold) and CD41 expression (91%) achieved in this experiment shows the importance of the microenvironment and the cell-to-cell signaling during megakaryocyte expansion.

Example 3

Driving Proplatelet Formation with the Cytokine SDF-1α

The cytokine SDF-1α mobilizes the mature megakaryocyte out of the bone marrow niche and is used to transition the mature megakaryocytes into an optimal culture environment. Initially, the cells are physically transferred from the maturation culture to a new culture dish containing SDF-1α within a 3D matrix. The SDF-1α lures the mature megakaryocytes into the 3D matrix. Exemplary 3D matrices include, but are not limited to, gelatin, MATRIGEL®, ALGIMATRIX®, polystyrene, and polyester mesh. The effects on megakaryocyte survival and proplatelet formation are measured. The proplatelet formation matrix is then subjected to conditions suitable for proplatelet formation.

Example 4

Driving Proplatelet Formation with Extracellular Signals

Figure 5A:
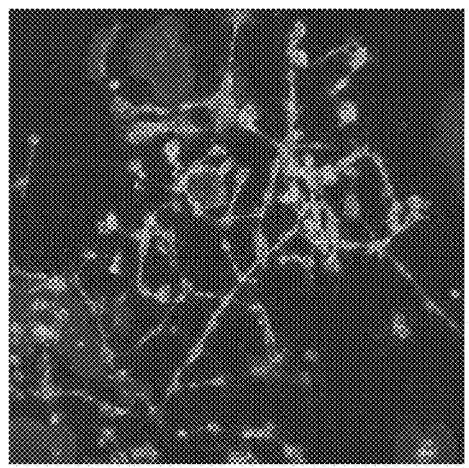
FIGS. 5A-C depict proplatelet formation and platelet release from mature megakaryocytes.
Figure 5B:
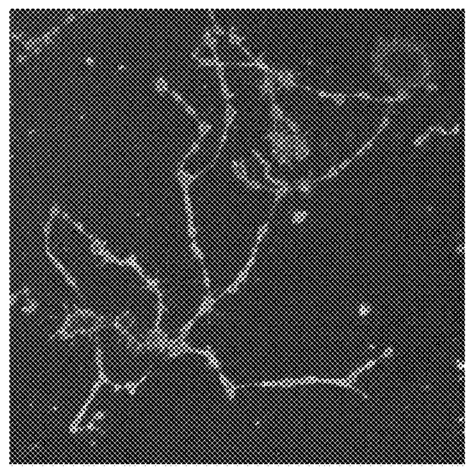
Figure 5C:
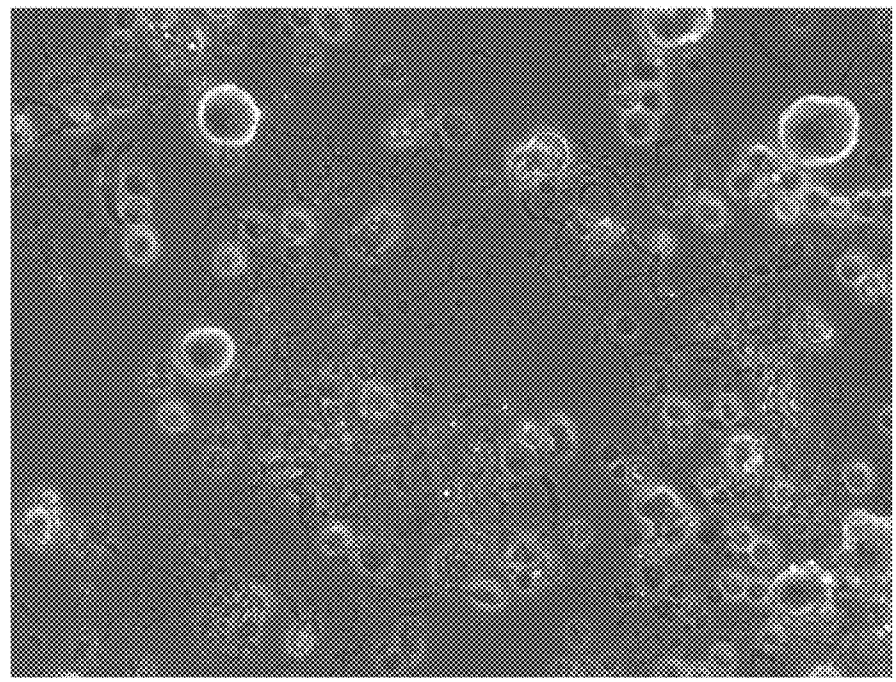
Figure 6:
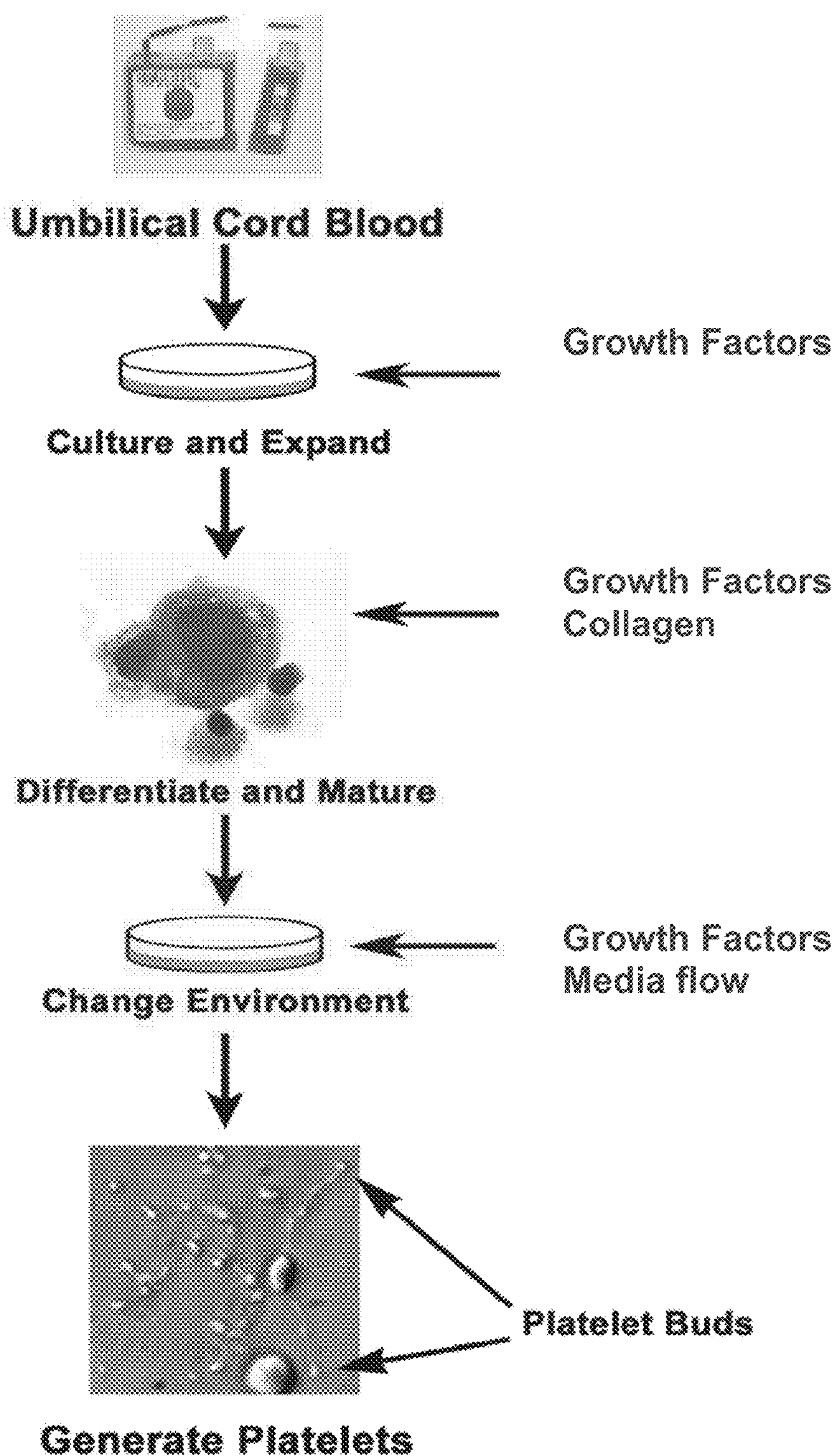
FIG. 6 depicts a flow diagram of one embodiment of the disclosed method for producing platelets in vitro.

Extracellular matrix proteins and other factors are introduced into the proplatelet formation culture environment to simulate the vascular niche. These proteins include, but are not limited to, fibrinogen, fibronectin, vWF, Fas-ligand, PMA, nitric oxide, Rho/Rock inhibitors, Src inhibitors, Rac1 activator, Cdc42 activator, MLCK inhibitors, hirudin, heparin, and c-Myc inhibitors. Each of these factors increases both the proportion of megakaryocytes producing proplatelets and the number of processes per megakaryocyte. Membranes with pores between 3 μm and 5 μm are coated with these reagents and the megakaryocytes are stimulated to release proplatelets and platelets through the pores. FIGS. 5A-C depicts extended proplatelets budding from the mature megakaryocytes and platelets being released after contact with fibrinogen.

Example 5

Umbilical Cord Blood CD34+ Cell Culture

Introduction: To address the need for a reliable supply of platelets in desirable quantities, a defined, serum-free culture method was designed using a novel bioreactor to increase the yield of platelets from stem cell-derived megakaryocytes.

Methods: CD34 cells isolated from umbilical cord blood were expanded with a variety of reagents and on a nanofiber membrane using serum-free medium. These cells were then differentiated into megakaryocytic lineage by culturing with thrombopoietin and stem cell factor in serum-free conditions. Polyploidy was induced by addition of Rho kinase inhibitor or actin polymerization inhibitor to the CD41 cells. A novel bioreactor was developed that recapitulated aspects of the bone marrow vascular niche. Polyploid megakaryocytes that were subjected to flow in the bioreactor extended proplatelets and shed platelets, as confirmed by light microscopy, fluorescence imaging, and flow cytometry.

Results: CD34+ cells were expanded 200-fold. CD41+ cells were expanded 100-fold. An average of 100 platelets per input megakaryocyte was produced from the bioreactor, for an overall yield of $10^6$ platelets per input CD34+ cell. The platelets externalized p-selectin following activation.

Discussion: Several steps along the biological pathway from stem cell to platelet can be quantity limiting. For example, expansion of CD34 cells early in the culture process will have a greater impact on final cell number than expansion of later, more differentiated cells. Accordingly, the present author divided the process of megakaryocyte biogenesis and platelet production into modules focusing on those quantity-limiting steps. Quantity limiting steps include CD34 cell expansion, immature megakaryocyte expansion, polyploidization, and platelet release. This example addresses each of these steps individually and then assembles them into a production line to achieve high platelet yields. The result is a novel, stepwise culture method and bioreactor that have the capability of producing clinically relevant numbers of platelets.

Materials and Methods:

Umbilical Cord Blood CD34 Isolation and Expansion

Umbilical cord blood units not suitable for clinical use were obtained from the New York Blood Center National Cord Blood Bank, where they were collected after informed consent in accord with the Declaration of Helsinki. Isolation of umbilical cord blood CD34 cells was performed using either a positive selection or a negative selection method. The positive selection method used has been described in G. Mattia et al., *Different ploidy levels of megakaryocytes generated from peripheral or cord blood CD34+ cells are correlated with different levels of platelet release,* 99(3) BLOOD 888 (February 2002). Briefly, mononuclear cells were layered on a Ficoll-Hypaque gradient (GE Healthcare, Barrington, Ill.), washed twice with phosphate-buffered saline (PBS) (Life Technologies) supplemented with 5% fetal bovine serum (FBS) (Life Technologies). To purify CD34 cells, the mononuclear selection fraction was subject to two cycles of immunomagnetic bead separation using a MINIMACS CD34 isolation kit (Miltenyi Biotech, Auburn, Calif.), according to manufacturer's recommendations. The purity of the sample ranged from 70% to 90% CD34 positive and was approximately 30% CD41 positive based on flow cytometry analysis.

The negative selection method was based on previously described methods where umbilical cord blood-derived CD34 cells were enriched by a negative selection method with the use of ROSETTESEP (Stem Cell Technologies, Vancouver, Canada). M. P. Avanzi et al., *Optimizing megakaryocyte polyploidization by targeting multiple pathways of cytokinesis,* 52(11) TRANSFUSION 2406 (November 2012). Briefly, cells were washed with phosphate buffered saline (PBS, Life Technologies) and incubated with ROSETTESEP reagent for 10 min at room temperature. Next, cells were layered on a Ficoll-Hypaque gradient, washed twice with phosphate-buffered saline. The final product was approximately 20% to 30% CD34 positive and 30% CD41 positive.

UCB derived CD34 enriched cells were plated at a density of $1\times10^4$ per well (24 well plate) in suspension culture and combined with one of the following reagents: STEM REGENIN-1 (StemCell Technologies, Vancouver, BC), 0.75 μM; copper chelator tetraethylenepentamine, 5 μM (TEPA) (Sigma Aldrich, St Louis, Mo.); or zVADfmk, 100 nM (Abcam, Cambridge, Mass.). Reagents were added with culture medium and cytokine cocktail on day 0, 4, 7 and 10 of culture. Additionally, in separate experiments, CD34 enriched cells were expanded on NANEX nanofiber membranes (Arteriocyte, Cleveland Ohio). The membranes were adherent to the bottom of wells in 24 well tissue culture plates. Cells were plated on the membrane at 1,000 cells per well on the first day of culture and reagents were added as above. Serum-free media were utilized for all CD34 expansion steps consisting of STEMSPAN SFEM medium (StemCell Technologies) supplemented with SCF, TPO and FLT3-ligand, all at 50 ng/ml.

Megakaryocyte Differentiation

Culture expanded CD34 cells were plated in 24 well tissue culture plates at $1\times10^4$ cells/ml in STEMSPAN SFEM medium with 50 ng/ml thrombopoietin (TPO) (Millipore, Temecula, Calif.) and 5 ng/ml Stem Cells Factor (SCF) (Millipore) to induce megakaryocytopoiesis. Medium (StemSpan SFEM) and TPO (50 ng/ml) were added on day 8, keeping the cell concentration below $1\times10^6$/mL, and cells were cultured for another 3 or 4 days.

Induction of Polyploidization

At the completion of the megakaryocyte differentiation stage on day 8, megakaryocytes were stimulated to undergo polyploidization by adding either the actin polymerization inhibitor, latrunculin (Santa Cruz Biotechnologies, Dallas, Tex.), at a final concentration of 10 μg/ml, or the Rho-kinase inhibitor, Y27632 (Sigma Aldrich, St. Louis, Mo.), at 10 μM, and then culturing the cells for an additional 3 or 4 days.

Bioreactor

A novel bioreactor was developed for efficiently harvesting platelets via shear flow from megakaryocytes resting on a pseudo-3D membrane. The bioreactor design was essentially a membrane sandwiched between two flow chambers. The membrane was either the NANEX nanofiber membrane (Arteriocyte, Cleveland, Ohio), or a PALL 5 μM PVC filter from (PALL, Port Washington, N.Y.). Initial prototypes were constructed from modified commercially available flow chambers: an IBIDI I-SLIDE VI 0.4 (Ibidi, Munich, Germany) and a 3DKUBE (Kiyatec, Greenville, S.C.). Final versions were printed on a 3D printer (MAKERBOT, MakerBot, Brooklyn, N.Y.). The upper chamber housed the megakaryocytes, and the lower chamber was a flow chamber for harvesting of platelets. Medium flowed from the top chamber through the membrane to the lower chamber, perpendicular to the membrane. At the same time, medium flowed through the lower chamber parallel to the membrane surface. Flow from the top chamber and flow through the lower flow chamber were achieved via syringe pump at initial shear rates of 30 $s^{-1}$ to 70 $s^{-1}$. Shear rates at the membrane surface were calculated using Son's method for calculating the relative shear in a rectangular flow channel. Younggon Son, *Determination of shear viscosity and shear rate from pressure drop and flow rate relationship in a rectangular channel,* 48 Polymer 632 (2006).

Flow Cytometry for CD34+ and Megakaryocyte Counting

All flow cytometry experiments where performed with a BD FACS LSR FORTESSA machine (Becton Dickinson, San Jose, Calif.) and analyzed with BD FACSDIVA software (Becton Dickinson). Cells were washed and resuspended in PBS with 5% FBS and incubated with either FITC-labeled anti-CD34 antibody (Becton Dickinson) or a combination of Alexa 647-labeled anti-CD41 antibody and FITC-labeled anti-CD42b antibody (Becton Dickinson). Labeled cells were then analyzed and counted.

Flow Cytometry for Megakaryocyte Ploidy

Megakaryocyte ploidy was analyzed on day 11 of culture. Cells were labeled with Alexa 647-conjugated anti-CD41 antibody, incubated for 20 min on ice, fixed with 4% paraformaldehyde (Fisher Scientific) for 15 minutes and then washed with PBS. Next, cells were permeabilized with methanol 75% (Sigma Aldrich) for 1 hour at 4° C. and washed with PBS+BSA, 2%+NP40, 0.05% (Fischer Scientific) solution. Finally cells were treated with Propidium Iodide/RNase solution (Becton Dickinson) and incubated for 30 minutes in the dark at room temperature before flow cytometry analysis.

Proplatelet Formation Quantification

Proplatelet formation was quantified on day 11 of culture using a grid strategy, as previously described by M. P. Avanzi et al., *Rho kinase inhibition drives megakaryocyte polyploidization and proplatelet formation through MYC and NFE2 downregulation,* 164(6) Br. J Haematol. 867 (March 2014). Briefly, using an inverted light microscope (Olympus CKX41) 10 random-field images were acquired at 40× magnification from each well. All megakaryocytes present on each field were counted. A counting grid with 25 μm squares was used to enumerate the number of proplatelet processes. Each proplatelet segment inside each square was counted and the sum of all segments in 10 random field images (40× magnification) was used for comparison. From these numbers, a measure of proplatelet density per cell per unit area was generated and used to compare the results of different culture conditions.

Platelet Count Assessment

Platelets were counted manually and using the automatic cell counter ADVIA 120 (Siemens, Tarrytown, N.Y., USA).

Platelet Morphological Analysis

Platelets collected were cytospun onto glass slides precoated with Poly-L-Lysine (Fisher Scientific), stained with Wright-Giemsa (Fisher Scientific) and observed with a Leica inverted contrasting microscope fitted with a camera DFC420 (Leica Camera Inc, Allendale, N.J.)

Platelet Surface Expression of P-Selectin

Platelets collected from the bioreactor were tested for their function based on the externalization of P-Selectin after activation with phorbol myristate acetate (PMA) using flow cytometry. Platelets were collected in eppendorf tubes, labeled with Alexa 647-conjugated anti-CD41 antibody, PE-conjugated anti-CD-62P (Becton Dickinson) and a live cell stain, Calcein AM (Sigma-Aldrich) for 15 min at room temperature. Next, platelets were activated using PMA (Sigma Aldrich) 10 μg/mL for 15 min at room temperature. Cells were then analyzed by flow cytometry for P-Selectin externalization. Anti-Y1-PE (Becton Dickinson) was used as an isotype control.

Results:

Expansion of CD34 Cells

UCB derived CD34 cells were expanded in combination with reagents previously reported to increase CD34 cell expansion, as well as on a pseudo-3D membrane. The aryl hydrocarbon signaling inhibitor SR-1, copper chelator tetraethylenepentamine (TEPA), and caspase inhibitor zVAD-fmk, have been shown to increase the CD34 fold expansion in vitro. The present author found that the use of the aryl hydrocarbon receptor inhibitor (SR-1) increased the CD34 fold expansion to a mean of 85 fold at day 7 (FIG. 9A). However, this was not significantly different from the control culture that achieved a mean of 40-fold expansion by day 7 (n=3). TEPA and zVADfmk resulted in 19 fold and 25 fold expansion of CD34 cells, respectively on day 7. Further culture did not increase the final number of CD34 cells. Culturing cells on the NANEX membrane resulted in a significant increase in CD34 cell expansion. The membrane supported CD34 expansion to greater than 100-fold maximum expansion (mean 87-fold) compared to control (mean 57-fold, p=0.05, n=3) (FIG. 9B). Next both the membrane culture and the SR-1 were combined. Combining the 3D substrate with the aryl hydrocarbon signaling inhibitor significantly increased the CD34 expansion up to a maximum 200-fold (mean 120-fold), compared to control (p=0.01, n=3) (FIG. 9B). These show the high degree of expansion of CD34 cells obtainable from umbilical cord blood.

Differentiation and Expansion of Megakaryocytes

The expanded CD34 cells were cultured to differentiate into megakaryocytes, as defined by staining positive for both CD41 and CD42b. Megakaryocytes cultured from negatively selected CD34 cells had greater expansion than those from positively selected CD34 cells (p=0.002, n=5) (FIG. 10A). This serum-free negative selection and culture resulted in a 100-fold expansion of cells that were 64% (maximum 90%) CD41 and 60% CD42b positive on day 8 (FIG. 10B). Megakaryocytes cultured and expanded with SCF and TPO on a 3D matrix for the entire period of culture showed the highest expansion rates, reaching 200 fold (FIG. 10C). These experiments show that CD41 cells can be expanded from cultured cord blood CD34 cells using a simple medium and a pseudo-3D growth environment.

Polyploidization

The present author theorized that higher ploidy cells would release more platelets in vitro. High ploidy was achieved in megakaryocytes by inhibiting cleavage furrow formation by treating day 8 megakaryocytes with either the Rho kinase inhibitor, Y276329, or the actin polymerization inhibitor, latrunculin. Megakaryocytes treated once on day 8 of culture had the same increase in ploidy as those treated daily on days 8 through 11, so only one treatment day was used. After treatment with either Y27632 or latrunculin, 30% of megakaryocytes had ploidy >8 on day 11, compared to less than 10% of controls (p=0.007, n=3) (FIGS. 11A-11C). Peaks representing up to 64N were observed. These high ploidy megakaryocytes also went on to generate significantly more proplatelets than control megakaryocytes (p=0.02, n=3) (FIGS. 11D-11F). These experiments show that high ploidy, proplatelet-producing megakaryocytes can be generated in a synchronized manner from cultured cord blood CD34 cells.

Platelet Production and Collection

A bioreactor was developed to both mimic the bone marrow perivascular space, and accommodate large numbers of megakaryocytes. The megakaryocytes were grown in a synchronized manner and introduced to the bioreactor all at once, in distinction to previously reported bioreactors in which megakaryocytes were loaded over time. The bioreactor consisted of an upper chamber where the megakaryocytes sit on the surface of a membrane, and a lower chamber beneath the membrane that is subjected to flow (FIG. 12A). Since the membrane that had supported both CD34 expansion and megakaryocyte expansion had micron-scale spaces between their constituent fibers, it was tested and found to function in the reactor. Megakaryocytes seeded into the upper chamber and subjected to flow extended processes through the membrane into the lower chamber (FIG. 12B). This process was not completely dependent on flow through the membrane, since megakaryocytes seeded onto a membrane without flow also extended processes into the membrane (FIG. 12C). Platelet like particles were recovered from the lower chamber (FIG. 12D). A shear rate of 30 $s^{-1}$-70 $s^{-1}$ in the lower chamber yielded an average of 100 platelets per input megakaryocyte, while a shear rate of 200 $s^{-1}$ yielded no platelets. Constant flow through the membrane from the upper to the lower chamber at 0.1 ml/min was required to produce platelets, since experiments without flow through the upper chamber yielded no platelets. A 5 μM PVC filter from Pall was also functional in the bioreactor. Flow through the bioreactor lasted 30 min for each experiment. For these studies 10,000 megakaryocytes were seeded into the bioreactor and the platelet output was 1-3×$10^6$ per experiment (n=15).

Platelet Characterization

Platelets retrieved form the bioreactor were characterized by flow cytometry, by a flow cytometry-based cell analyzer, and by morphology. Cells collected from the bioreactor were labeled with a live-cell stain and a fluorescently labeled anti-CD41 antibody, and then identified by double positive staining for live-cell and CD41 on flow cytometry. p-selectin expression was also measured before and after phorbol myristate acetate (PMA) stimulation as a measure of activation, and revealed that 25% of the particles expressed p-selectin at baseline, while 65% expressed p-selectin after PMA stimulation (FIG. 12E).

The ADVIA cell analyzer recognizes platelets by both shape and refractive index, or "mean platelet component," that distinguishes between platelets and red blood cell fragments. This machine identified the particles released from the bioreactor as "platelets." Cells from the bioreactor were cytospun and stained with Wright-Giemsa for morphology. This revealed numerous platelet-like particles with granular-appearing contents (FIG. 12D).

CONCLUSIONS

Figure 13:
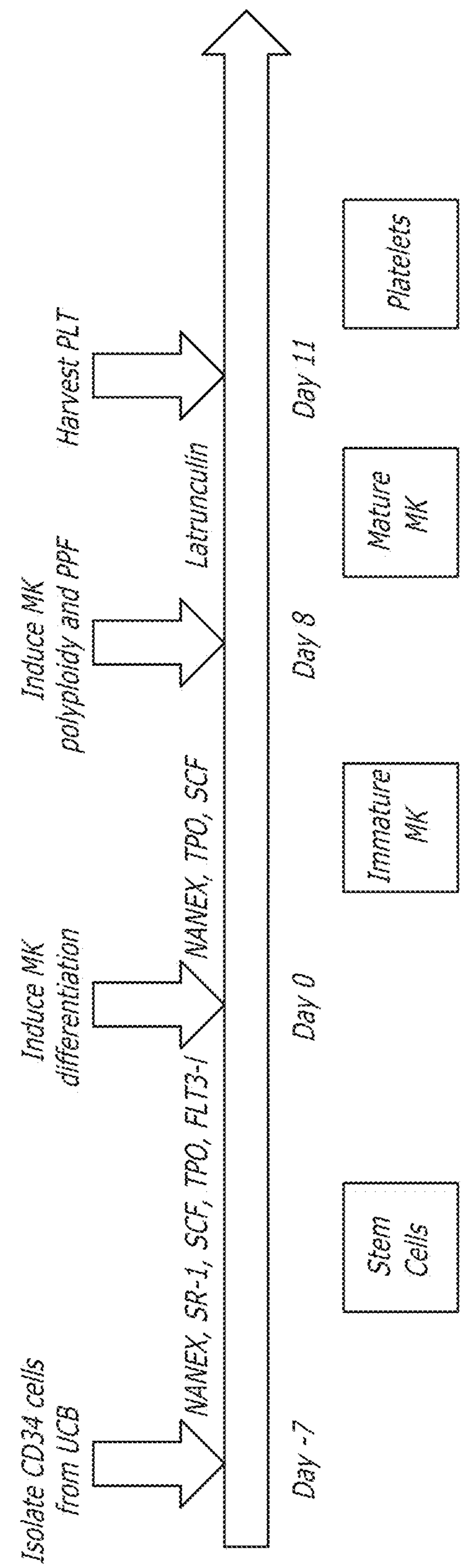
FIG. 13 is a schematic of process to generate platelets. Day −7: CD34 cells are enriched from cord blood by negative selection and expanded for 7 days. Day 0: the expanded cells are transferred to MK-inducing culture medium for another 8 days. Day 8: cells are induced to undergo polyploidy. Day 11: cells are introduced into the bioreactor and platelets are collected.

In this example a method was designed to recapitulate the stages of megakaryocyte differentiation and maturation, and a bioreactor was designed to emulate some of the characteristics of the perivascular bone marrow microenvironment (FIG. 13). The current model of platelet production in the bone marrow begins with megakaryocytes migrating to the sinusoid blood vessels of the bone marrow and nestling around them, in contact with extracellular matrix proteins such as fibrinogen and von Willebrand factor. This contact induces the megakaryocytes to protrude long pseudopodial processes, called proplatelets, through the vessel walls and into circulation. Intravital microscopy has documented this process and also revealed that larger segments of megakaryocytes may enter the sinusoids as well. The shear force of the blood flow presumably particulates the proplatelet processes into platelets. Each megakaryocyte is estimated to produce over 1,000 platelets in this manner.

By addressing each rate-limiting step in thrombopoiesis individually, a production line has been assembled for ex-vivo platelet production from umbilical cord blood. This method resulted in 100-fold expansion of CD34 cells, 100-fold expansion of megakaryocytes from CD34 cells, and 100-fold expansion of functional platelets from those megakaryocytes. Thus, altogether this method can achieve 106-fold expansion of platelets from the input stem cells. These results demonstrate the feasibility of a scalable process for generating platelets from stem cells in numbers sufficient for clinical use.

It is contemplated that membranes other those disclosed in this experiment will achieve similar results. Moreover, in some embodiments, the membranes are coated with extracellular matrix protein. In some embodiments, they are no so coated. Moreover, some embodiments employ different flow rates and flow chamber designs, and in some embodiments megakaryocytes are derived from a source other than umbilical cord blood.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. In one embodiment, the terms "about" and "approximately" refer to numerical parameters within 10% of the indicated range.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A platelet production device for the ex vivo production of platelets comprising:

a fluid source, the fluid comprising a growth medium;

a platelet production chamber in fluid communication with the fluid source, the chamber comprising a first and a second fluid flow path, the first and second fluid flow paths separated from each other within the chamber by a scaffold permeable to proplatelet processes;

wherein the permeable scaffold allows at least a portion of the fluid in the first fluid flow path to permeate the permeable scaffold toward the second fluid flow path causing a plurality of megakaryocytes located in the first fluid path to extend their respective proplatelet processes through the permeable scaffold toward the second fluid flow path;

wherein the platelet production device transports fluid from the fluid source into the platelet production chamber; and wherein the second fluid flow path brings the growth medium into contact with at least a portion of the permeable scaffold to remove at least some platelets from the proplatelet processes.

2. The platelet production device of claim 1 further comprising a platelet collection chamber.

3. The platelet production device of claim 1, wherein the growth medium flows through the platelet production chamber at a volumetric flow rate of between about 15 ml/min and about 55 ml/min.

4. The platelet production device of claim 1, wherein the growth medium exhibits a shear rate at an interface with the permeable scaffold that is between about 10 $s^{-1}$ and about 100 $s^{-1}$.

5. The platelet production device of claim 1, wherein the growth medium exhibits a shear rate at an interface with the permeable scaffold that is at least about 30 $s^{-1}$.

6. The platelet production device of claim 1, wherein the growth medium exhibits a shear rate at an interface with the permeable scaffold that is less than about 70 $s^{-1}$.

7. The platelet production device of claim 1, wherein the permeable scaffold has a thickness of between about 100 μm and about 200 μm.

8. The platelet production device of claim 1, wherein the permeable scaffold includes pores that are between about 2 μm and about 5 μm in diameter.

9. The platelet production device of claim 1, wherein the growth medium follows both the first and the second fluid flow paths.

10. The platelet production device of claim 9, wherein the flow rate of the growth medium through the first flow path is less than the flow rate of the growth medium through the second flow path.

11. The platelet production device of claim 9, wherein the flow rate of the growth medium through the first flow path is sufficient to hold at least some of the plurality of megakaryocytes against the permeable scaffold and to compel at least some of the proplatelet process of the megakaryocytes to grow in the direction of the second fluid flow path.

12. A method of growing and harvesting platelets from proplatelet processes, the method comprising:

providing a production device for the ex vivo production of platelets, the production device comprising:

a fluid source, the fluid comprising a growth medium;

a platelet production chamber in fluid communication with the fluid source, the chamber comprising a first and a second fluid flow path, the first and second fluid flow paths separated from each other within the chamber by a permeable scaffold which allows at least some of the fluid in the first fluid flow path to permeate the permeable scaffold toward the second fluid flow path and is permeable to proplatelet processes, the permeable scaffold prevents a mature megakaryocyte from passing through;

pumping the growth medium through at least one of the first and second flow paths;

providing a plurality of megakaryocytes within the first fluid flow path so as to position the megakaryocytes against the permeable scaffold and direct their respective proplatelet processes in the direction of the second fluid flow path;

removing the growth medium from the second flow path after it has interacted with the permeable scaffold so as to remove platelets from the proplatelet processes; and harvesting the platelets from the removed growth medium.

13. The method of claim 12, wherein the growth medium flows through the platelet production chamber at a volumetric flow rate of between about 15 ml/min and about 55 ml/min.

14. The method of claim 12, wherein the growth medium exhibits a shear rate at an interface with the permeable scaffold that is between about 10 $s^{-1}$ and about 100 $s^{-1}$.

15. The method of claim 12, wherein the growth medium exhibits a shear rate at an interface with the permeable scaffold that is at least about 30 $s^{-1}$.

16. The method of claim 12, wherein the growth medium exhibits a shear rate at an interface with the permeable scaffold that is less than about 70 $s^{-1}$.

17. The method of claim 12, wherein the permeable scaffold has a thickness of between about 100 μm and about 200 μm.

18. The method of claim 12, wherein the permeable scaffold includes pores that are between about 2 μm and about 5 μm in diameter.

19. The method of claim 12, wherein the system is configured so that the growth medium follows both the first and the second fluid flow path.

20. The method of claim 19, wherein the flow rate of the growth medium through the first flow path is less than the flow rate of the growth medium through the second flow path.

* * * * *